United States Patent [19]

Hagen

[11] Patent Number: 5,075,227
[45] Date of Patent: Dec. 24, 1991

[54] DIRECTIONAL CLONING

[75] Inventor: Frederick S. Hagen, Seattle, Wash.

[73] Assignee: ZymoGenetics, Inc., Seattle, Wash.

[21] Appl. No.: 320,191

[22] Filed: Mar. 7, 1989

[51] Int. Cl.$^5$ .................. C12N 15/00; C12N 15/10; C12N 15/70; C12P 19/34
[52] U.S. Cl. .................. 435/172.3; 435/91; 435/320.1; 935/18; 935/26; 935/27; 935/29; 935/31; 935/56; 935/58
[58] Field of Search .................. 435/172.3, 172.1, 91, 435/320.1; 935/8, 6, 16-18, 22-24, 26-31, 36-41

[56] References Cited

U.S. PATENT DOCUMENTS 4,342,832 8/1982 Goeddel et al. .................. 435/172.3

OTHER PUBLICATIONS

Belyavsky, A. et al., 1989, Nucleic Acids Research, vol. 17, No. 8, pp. 2919-2932.
Belyaskii, A. V. et al., 1988, Dokl. Acad. Nauk SSSR, vol. 303, No. 6, pp. 1498-1501, and Chem. Abst. 1989, vol. 110, No. 17, p. 229, Abstr. 149153.
Sanger, F. et al., 1975, Journal of Molecular Biology, vol. 94, pp. 441-448.
Palazzolo, M. J. et al., 1987, Gene, vol. 52, pp. 197-206.
Promega Corporation, 1988/1989 Catalog and Applications Guide, 1988, Promega Corporation, Madison, Wisconsin, Section 12, p. 7.
Maniatis, T. et al., 1982, *Molecular Cloning A Laboratory Manual*, Cold Spring Harbor Laboratory, pp. 118, 119, 222.
Pharmacia Molecular Biologicals Catalog, 1986, Pharmacia, Piscataway, New Jersey, pp. 70, 72, 75, 82, 89.
Priess, H. et al.. 1980, Molecular and General Genetics, vol. 178, pp. 27-34.
Noma et al., Nature, 319:640-646, 1986.
Melton et al., Nuc. Acids Res., 12:7035-7056, 1984.
Dunn and Studier, J. Molec. Biol., 166:477-536, 1983.

Primary Examiner—Richard A. Schwartz
Assistant Examiner—Mary E. Mosher
Attorney, Agent, or Firm—Seed and Berry

[57] ABSTRACT

Methods for cloning cDNA and producing mRNA from the cloned cDNA are disclosed. The cDNA is cloned in one orientation through the use of a vector containing a directional cloning site and through the use of primer-adapter sequences complementary to portions of the directional cloning site. The vector may also contain a promoter, one or more terminators and a polyadenylation signal to facilitate transcription of the cloned cDNA and translation of the mRNA.

66 Claims, 9 Drawing Sheets

DIRECTIONAL CLONING

TECHNICAL FIELD

The present invention relates to methods for preparing cDNA and messenger RNA and to vectors useful therein.

BACKGROUND OF THE INVENTION

The production of complementary DNA (cDNA) molecules from messenger RNA (mRNA) has allowed the isolation, characterization and expression of a large number of genetic sequences. The use of cDNA permits the production of higher eukaryotic proteins in microbial hosts, and is therefore central to the genetic engineering industry.

Numerous methods for producing cDNA have been described. For a general discussion of cDNA cloning methods, see Maniatis et al. (*Molecular Cloning: A Laboratory Manual*, Cold Spring Harbor Laboratory, Cold Spring Harbor, N.Y., 1983). In general, the common features of cDNA cloning strategies include isolation of mRNA, annealing of the mRNA to relatively short DNA primers followed by enzymatic synthesis of the first and second strands of DNA. The resulting double stranded molecules are inserted into a plasmid or bacteriophage vector and transformed into a host cell, generally the bacterium *E. coli*, to produce a "library" of cDNA molecules. The library is then screened by a variety of methods to identify clones of interest.

Early methods for producing cDNA were not well suited to cloning sequences corresponding to low-abundance messages, and often yielded incomplete clones. These methods relied on the use of the first cDNA strand as a primer for second strand synthesis, resulting in the formation of a hairpin loop which had to be removed by nuclease digestion. This digestion, together with premature termination of first strand synthesis, resulted in the cloning of incomplete cDNAs. Cloning of the entire coding sequence for a rare protein could therefore be extremely laborious, if not impossible, requiring many rounds of cloning and screening, then joining of cloned fragments to generate the complete sequence.

More recently, a number of methods have been described which produce a higher yield of full-length clones and are more suited to the cloning of rare sequences. These methods rely on enrichment for desired sequences or priming strategies which eliminate the need for nuclease treatment. Despite the advances represented by these methods, certain problems remain, including difficulty in cloning rare sequences that encode proteins known only by their intrinsic activities, which may require full-length, expressible cDNAs.

The need to efficiently express cloned sequences in order to identify clones of interest has led to the development of directional cloning techniques, whereby cDNA sequences are inserted into cloning vectors in a predetermined orientation. By providing transcriptional promoter and terminator sequences adjacent to the insertion site in the cloning vector, cloned sequences can be expressed, permitting screening of clones by detection of the gene product of interest. These directional cloning methods generally rely on the use of vector and cDNA sequences constructed with specific, complementary termini to obtain the desired insertion. Okayama and Berg (*Mol. Cell. Biol.* 2: 161–170, 1982) describe a cloning method in which a dT-tailed plasmid serves as a primer for first strand cDNA synthesis, and a primer-adapter is used for second strand synthesis. Shortcomings of this system include its complexity, the difficulty of preparing the vector components, and the inability to easily size fractionate the cDNA. The complexity of the system is evidenced by the numerous steps required to synthesize the cDNA and introduce the primer-adapter into the cDNA-vector construct. Preparation of the vector components is a multi-step process involving two physical separations, gel electrophoresis and affinity chromatography, which cause large losses of material, therefore necessitating the need for large starting amounts of vector and the use of large amounts of reagents. Even under optimum conditions, a fair amount of less than full-length cDNA is synthesized. The method of Coleclough et al. (*Gene* 34: 305–314, 1985) utilizes primer-adapters which are complementary to the ends of the cloning vector. Preparation of the vector requires a number of manipulative steps, and second strand cDNA synthesis is completed on the vector-cDNA complex. With such a complex, it is difficult to reproducibly carry out second strand synthesis with good efficiencies of cloning. Schmid et al. (*Nuc. Acids Res.* 15: 3987–3996, 1987) disclose a method utilizing specific primers to produce restriction site sticky ends on the cDNA insert. However, primer design is based on foreknowledge of the target sequence, limiting this method to the cloning of previously cloned DNAs. The method of Meissner et al. (*Proc. Natl. Acad. Sci. USA* 84: 4171, 1987) requires endonuclease digestion of the double-stranded cDNA to allow insertion into the vector. Sequences containing corresponding internal endonuclease cleavage sites would therefore be cleaved. As with the method of Coleclough et al., the method of Han et al. (*Biochemistry* 26: 1617–1625, 1987) requires synthesis of second strand cDNA on a complex of vector, cDNA, and adapter-primer. As previously mentioned, these are difficult procedures and therefore cloning efficiencies are extremely variable.

Most of the above-mentioned cloning methods do not allow amplification of the cloned cDNA by the polymerase chain reaction (PCR) (Scharf et al., *Science* 233: 1076, 1986; Saiki et al., *Science* 239: 487, 1988), which requires the presence of two primers in high concentration to initiate repeated rounds of DNA synthesis between the sites where the primers anneal. This is not possible in those procedures which require vector priming or synthesis of the second strand on a cDNA vector complex. Although the methods that use oligonucleotide primers could utilize PCR to amplify cDNA prior to attaching the cDNA to a cloning vector, these approaches are still limited by the need for endonuclease digestion of the cDNA prior to ligation to the cloning vector, and therefore carry the risk of digesting the coding sequence of the cDNA.

Consequently, there remains a need in the art for a cDNA cloning method that permits directional cloning of low-abundance messages at high efficiency, can further incorporate the use of PCR, is amenable to size fractionation of cDNA, obviates the use of endonucleases to tailor the cDNA for attachment to the cloning vector, and permits expression of the cDNA. The present invention provides such methods, as well as other, related advantages.

DISCLOSURE OF THE INVENTION

Briefly stated, the present invention provides a method for preparing a double-stranded DNA molecule containing double-stranded cDNA consisting of a sense strand and an anti-sense strand, each of the strands having a 5' end and a 3' end. Generally, this method includes the steps of (a) annealing mRNA to a first oligodeoxynucleotide primer of the sequence $X_1T_n$, wherein $X_1$ is a sequence of deoxynucleotide monophosphates other than deoxythymidine from about 3 to about 25 nucleotides in length, wherein T is deoxythymidine monophosphate and wherein n is an integer from 6 to 30, (b) extending $X_1T_n$ with reverse transcriptase to produce an anti-sense strand, (c) adding deoxynucleotide monophosphates to the 3' end of the anti-sense strand to produce deoxynucleotide-tailed DNA, (d) annealing the deoxynucleotide-tailed DNA to a second oligodeoxynucleotide primer of the sequence $X_2T_yN_m$, wherein $X_2$ is a sequence of deoxynucleotide monophosphates other than deoxythymidine from about 3 to about 25 nucleotides in length, wherein N is a deoxynucleotide monophosphate complementary to the deoxynucleotide tail on the anti-sense strand, wherein m is an integer from 6 to 30, wherein T is deoxythymidine monophosphate and wherein y is an integer greater than or equal to 1, (e) extending $X_2T_yN_m$ with DNA polymerase to produce double-stranded cDNA, (f) treating the double-stranded cDNA with a DNA polymerase having 3'-exonuclease activity in the presence of deoxyadenosine triphosphate to remove the portions of the 3' ends of the double-stranded cDNA which are complementary to $X_1$ and $X_2$, and (g) incubating the treated, double-stranded cDNA and a double-stranded linear vector in the presence of DNA ligase under conditions allowing hybridization and ligation of the cDNA and vector, the vector having 5' single-stranded termini sufficiently complementary to $X_1$ and $X_2$ to allow annealing under the incubation conditions, wherein $X_1$ and $X_2$ are non-palindromic, sufficiently noncomplementary to prevent them from annealing to each other and sufficiently different to anneal to the vector in the desired orientation. In a preferred embodiment, the 3' end of the anti-sense strand is tailed with deoxyguanosine and N is deoxycytidine monophosphate.

In a related aspect, the present invention provides a method for amplifying a population of mRNA molecules. The method generally includes the preparation of cDNA as described above using a vector containing a transcriptional promoter, such as a bacteriophage promoter or a eukaryotic promoter, positioned so as to be capable, after the incubating step, of initiating transcription from the sense strand of the cDNA. The vector may further contain one or more transcriptional terminators positioned so as to be capable, after the incubating step, of terminating transcription from the sense strand of the cDNA. In one embodiment, the annealed, double-stranded cDNA and vector are inserted into bacterial host cells and the cells are cultured under suitable conditions so that the cDNA is transcribed to produce mRNA. In another embodiment, the annealed, double-stranded cDNA and vector are inserted into bacterial host cells, the cells are cultured to amplify the cDNA and vector, the cDNA and vector are extracted from the host cells, and the cDNA is transcribed to produce mRNA. The cDNA may be transcribed in vitro. Alternatively, transcription may be carried out in vivo by inserting the extracted cDNA and vector into eukaryotic host cells and culturing the eukaryotic host cells so that the cDNA is transcribed.

These and other aspects of the present invention will become evident upon reference to the following detailed description and attached drawings.

BEST MODE FOR CARRYING OUT THE INVENTION

Figure 1:
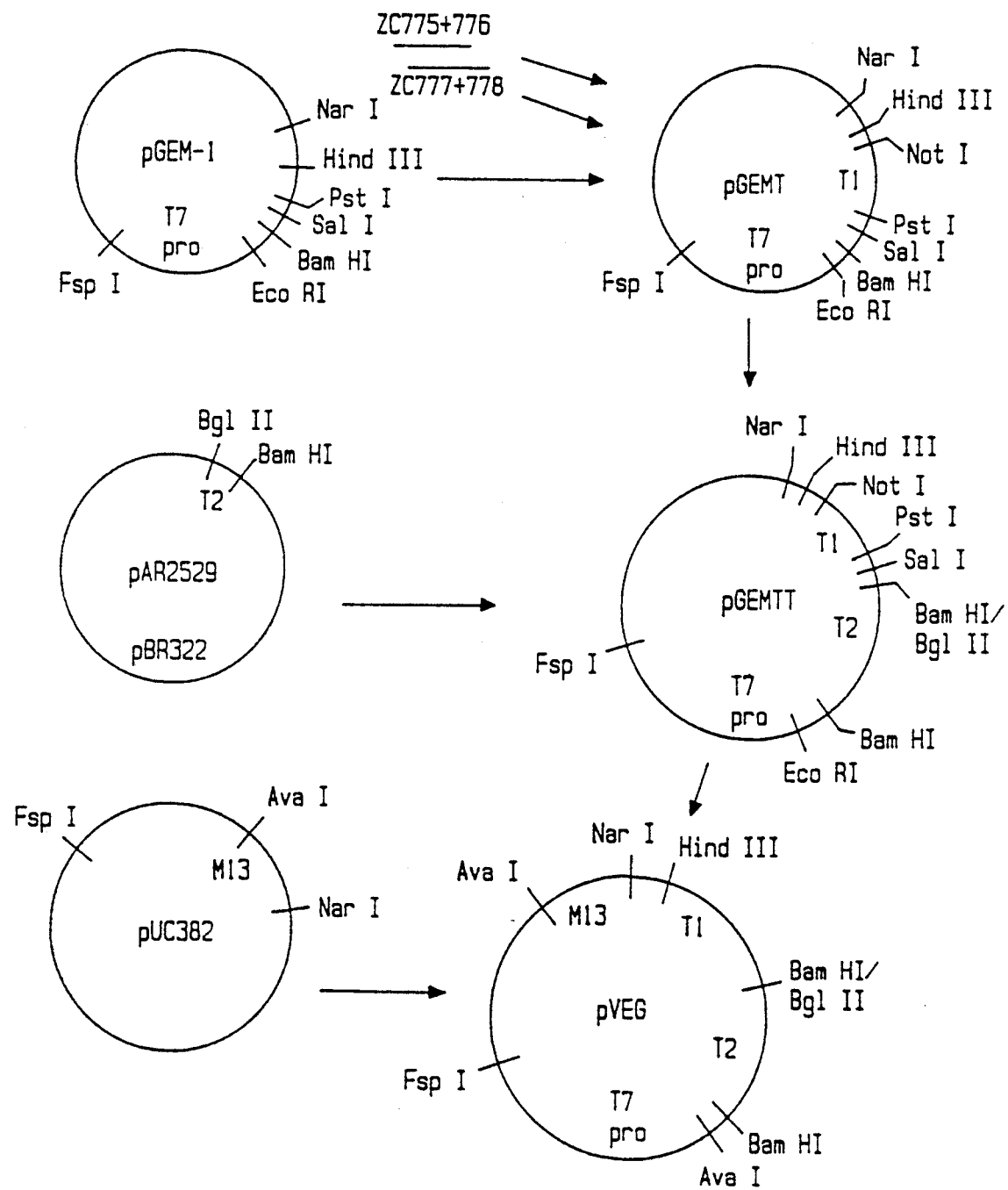
FIG. 1 illustrates the insert transcriptional terminators and the M13 intergenic region into the plasmid pGEM-1. T7 pro indicates the position of the bacteriophage T7 promoter. T1 and T2 indicate synthetic and native T7 terminators, respectively. M13 indicates the M13 intergenic region.

The present invention is directed to methods for the production of cDNA, transcription of the cDNA to produce mRNA, and to vectors useful within these methods. These methods are particularly suited to the cloning of rare sequences and facilitate the amplification and expression of those sequences.

According to the present invention, a double-stranded cDNA molecule is produced from mRNA by a series of steps including primer annealing and extension, tailing of first strand cDNA, primer annealing and extension to produce second strand cDNA, treatment of the double-stranded cDNA to produce termini complementary to the ends of a cloning vector, and hybridization and ligation of the treated cDNA and the vector. Insertion of the cDNA into the vector in a predetermined orientation is facilitated by the use of a novel class of primers. The presence of a transcriptional promoter adjacent to the cloning site in the vector and the design of the vector and insert ends permits transcription of the cloned DNA. Thus, the invention further provides for the production of mRNA corresponding to the cloned cDNA. The cloning methods of the invention can be combined with other techniques to select or enrich for gene sequences of interest.

The first (anti-sense) strand of the cDNA is synthesized from a mRNA template using a primer which hybridizes to the poly(A) tail of the mRNA. RNA is isolated from a suitable source according to conventional methods, for example that of Chirgwin et al. (*Biochemistry* 18: 52–94, 1979). In many instances it will be preferable to enrich for poly (A)+RNA (e.g. by oligo-d(T) cellulose chromatography), which may be further enriched for sequences of interest, such as by size fractionation. When the methods of the present invention are combined with the PCR technique, the RNA need not be enriched for poly (A)+sequences. The RNA is then annealed to an oligodeoxynucleotide primer of the sequence $X_1T_n$, wherein $X_1$ is a sequence of deoxynucleotides other than deoxythymidine from about 3 to about 25 nucleotides in length, preferably about 12 to about 15 nucleotides in length, and wherein $T_n$ is a sequence of deoxythymidine from about 6 to about 30, preferably about 15, nucleotides in length. Methods for producing oligonucleotides are well known in the art. A preferred method of oligonucleotide synthesis is automated synthesis using commercially available equipment, such as a Model 380A DNA synthesizer, available from Applied Biosystems (Foster City, CA). Alternatively, suitable oligonucleotides may be purchased from a number of suppliers. It is preferred to denature the RNA prior to first strand synthesis. In a preferred embodiment, the RNA and primer are heat denatured, generally at about 65° C. for about 2-4 minutes, and quickly chilled on ice. As will be understood by those skilled in the art, the exact time required for heat denaturation is dependent in part upon the volume of the solution and will be adjusted accordingly. The primer $X_1T_n$ is then extended with reverse transcriptase, such as AMV, MMLV or MMLV($H^{31}$) reverse transcriptase (available from Bethesda Research Laboratories, Gaithersburg, Md.), to produce the first (anti-sense) cDNA strand. Preferred conditions for first strand synthesis using AMV reverse transcriptase are essentially those described by Gubler and Hoffman (*Gene* 25: 263–269, 1983). Conditions for first strand synthesis using MMLV and MMLV($H^{31}$) reverse transcriptases are specified by the supplier.

Following extension of the primer to produce the first strand cDNA, it may be advantageous to hydrolyze the mRNA by treatment with alkali and to fractionate the cDNA. In a preferred embodiment, the cDNA is treated with 0.1 N KOH for 15 minutes at 65° C. and fractionated by alkaline agarose gel electrophoresis or by alkaline column chromatography. A preferred method of fractionation is Sepharose column chromotography in 50 mM KOH and 0.1 mM EDTA. These procedures remove the RNA template and small fragments of nucleic acid which might otherwise be tailed in the subsequent tailing reaction. In general, molecules of less than about 400 nucleotides will be removed, although this cutoff will be adjusted as necessary when cloning particularly long or short DNAs.

Alternatively, it may be preferable, after first strand synthesis, to allow the RNA template to remain as a hybrid with the cDNA, but to remove small nucleic acid fragments, such as primer and short (generally less than about 400 nucleotides) cDNA molecules. This may be accomplished by neutral agarose gel electrophoresis, neutral column chromatography or the neutral spin column method. The RNA-cDNA hybrid is then tailed using terminal deoxynucleotidyl transferase as described below.

The anti-sense strand is then tailed by the addition of deoxynucleotide monophosphates to the 3' end using the desired deoxynucleotide triphosphate and terminal deoxynucleotidyl transferase. Preferably, about 6–30 nucleotides will be added in the tail, most preferably about 10 to 15. Longer tails may reduce the efficiency of the cloning procedure and/or the expression of the cloned cDNA. The deoxynucleotides used in the tailing step can be deoxyadenosine (dA), deoxycytidine (dC), deoxyguanosine (dG) or deoxythymidine (dT) nucleotides, with dG preferred. dG-tailing provides the advantage of self-termination of the tailing reaction at about 15 bases.

The deoxynucleotide-tailed DNA is then used as a template for second (sense) strand synthesis. The tailed DNA is annealed to an oligodeoxynucleotide primer of the sequence $X_2T_yN_m$, wherein $X_2$ is a sequence of deoxynucleotide monophosphates other than dT from about 3 to about 25 nucleotides in length, preferably about 12 to about 15 nucleotides in length. To prevent incorrect hybridization in subsequent steps, $X_1$ and $X_2$ are different, non-palindromic sequences. $X_1$ and $X_2$ must be sufficiently noncomplementary to prevent them from annealing to each other as necessary for efficient cloning. In this regard, it will be evident to one skilled in the art that some degree of complementarity is acceptable, although a reduction in efficiency may be observed. $X_1$ and $X_2$ will also be sufficiently different from each other to prevent them from annealing to the single-stranded ends of the cloning vector in the wrong orientation during the cloning procedure. Preferably, $X_1$ and $X_2$ should be random sequences with no significant complementarity. Degree of complementarity may be determined using computer programs commonly used in the art (see, e.g., Pearson and Lipman, *Proc. Natl. Acad. Sci. USA.* 85: 2444–2448, 1988). As will be appreciated by those skilled in the art, the ability of two nucleotide sequences to anneal to each other can be determined by observation, such as by combining $X_1$ and $X_2$ under the conditions of the cloning reactions and determining the degree to which they anneal. $X_1$ and $X_2$ should have similar Tm when hybridized to complementary vector sequences. Determination of Tm is within the level of ordinary skill in the art and is described by Wallace et al. (*Nuc. Acid. Res.* 9: 879–894 1981). $T_y$ is one or more, preferably 2 or more, deoxythymidine monophosphates. $N_m$ is an oligodeoxynucleotide complementary to the deoxynucleotide tail on the tailed anti-sense strand, wherein m designates the length. If the anti-sense strand is tailed with dG, N will be dC. In general, $N_m$ will be from about 6 to about 30 nucleotides in length (i.e. m=6–30), preferably about 10 to 15 nucleotides in length (m=10–15), most preferably about 10 (m=10). It is preferable to have the tail of the cDNA be of approximately the same length as $N_m$. (Conditions of the tailing reaction are adjusted to provide a distribution of tail length around the desired length.) The annealed primer $X_2T_yN_m$ is then extended with a DNA-dependent DNA polymerase to produce double-stranded cDNA. Suitable DNA polymerase include *E. coli* DNA polymerase I, the Klenow fragment of *E. coli* DNA polymerase I, T7 DNA polymerase (including modified forms thereof, e.g., Sequenase ™, available from United Biochemical Corporation, Cleveland, Ohio) and Taq I DNA polymerase. Taq I polymerase is particularly preferred. Polymerases are available from a number of commercial suppliers, including Bethesda Research Laboratories (Gaithersburg, Md.), New England Biolabs (Beverly, Mass.) Perkin-Elmer Cetus (Norwalk, Conn.), Strategene (La Jolla, Calif.), Boehringer-Mannheim (Indianapolis, Ind.) and United States Biochemical Corporation (Cleveland, Ohio).

Following second strand synthesis, it is preferred to enrich for full-length DNA (e.g., by column chromatography).

The double-stranded cDNA is then treated with a DNA polymerase having 3'-exonuclease activity in the presence of deoxyadenosine triphosphate to remove the portions of the 3' ends of the DNA strands which are complementary to the primer sequences $X_1$ and $X_2$. Suitable polymerases in this regard include *E. coli* DNA polymerase I, the Klenow fragment of *E. coli* DNA polymerase I and T4 DNA polymerase. The use of T4 DNA polymerase is preferred. Inclusion of dATP in the reaction mixture results in termination of the 3'-to-5' exonuclease and polymerization reactions catalyzed by the polymerase at the $T_n$ and $T_y$ sequences in the primers, leaving 5' single-stranded overhangs containing the $X_1$ and $X_2$ sequences on the respective strands. Typically, this reaction is performed using 10 to 100 ng/µl of double-stranded cDNA, 33 mM Tris-acetate pH 7.9, 67 mM KAc, 10 mM MgAc, 0.1 mg/ml gelatin, 200 µM dATP, 5 mM DTT, and 0.1 U/µl T4 DNA polymerase (specifically tested to perform this reaction) in a reaction volume of 10 µl at 15° C. for 1 hour.

The treated, double-stranded cDNA is then annealed and ligated into a cloning vector. The vector is constructed so that upon cleavage it will have overhanging 5' termini equal to the lengths of $X_1$ and $X_2$ and of sufficient complementarity to $X_1$ and $X_2$ to allow annealing and ligation under the chosen reaction conditions. Complementarity may be determined by observation or computer analysis as discussed above. Although complete complementarity of $X_1$ and $X_2$ with the corresponding vector overhangs is not required, efficiency of annealing and ligation will generally reflect the degree of complementarity. Complementarity is most important near the ends of the single-stranded regions. In a typical annealing and ligation reaction, 167 ng/µl lambda vector, 1.7 to 7 ng/µl cDNA, 50 mM Tris pH 7.8, 5 mM MgAc, 1 mM ATP, 10 mM DTT, and 0.1 Weise units/µl of T4 DNA ligase are combined in a total volume of 3 µl and incubated for 2 hours at 37° C.

Cloning vectors for use within the present invention may be constructed according to standard procedures using readily available starting materials. Vectors useful in this regard include plasmids, bacteriophage vectors and other viral vectors, as well as vectors containing both plasmid- and virus-derived sequences. For example, hybrids of λ phage and plasmids provide a straightforward method of cloning cDNA in a λ vector and screening the cloned sequences in a eukaryotic host cell. Bacteriophage and plasmid vectors, including bacteriophage lambda vectors, plasmid pGEM-1 and other ColEl-based plasmids, have been described in the literature (Chang and Cohen, *J. Bact.* 134:1141–1156, 1978; Elhai and Wolk, *Gene* 68:119–138, 1988; Bolivar et al., *Gene* 2:95–113, 1977 and Vieira and Messing, *Gene* 19:259–268, 1982) and are available commercially (e.g., Promega Biotec, Madison, Wis.). In some instances it will be desirable to include multiple origins of replication in a cloning vector so that the vector can be used in more than one cell type. For example, the vector may contain both a bacterial and a mammalian origin of replication. For use within the present invention, a vector is cleaved at a restriction site, preferably a unique site, and ligated to an adapter sequence. It is preferred that, upon ligation, the adapter will not recreate the original restriction site at the vector-adapter junctions. The adapter contains an internal endonuclease site that is unique in the resultant vector and is bounded by sequences complementary to the sequences $X_1$ and $X_2$ on the cDNA insert. Transformation isolates are screened either by DNA sequence analysis or by specific oligonucleotide hybridization to obtain an isolate with the appropriate orientation for the adapter sequence. For use in cloning, the recircularized vector (containing the adapter) is digested at the unique site within the adapter and treated with T4 DNA polymerase in the presence of dTTP. This treatment results in 5' single-stranded overhangs to which complementary 5' overhangs on the cDNA insert can anneal. Preferred vectors include the vectors pVEGT', λVEGT', λgt11', pYcDE8' and pDVEG40, the construction of which is described in detail in the examples that follow. As will be apparent to the practitioner of ordinary skill in the art, equivalent vectors can be constructed by following the general procedures described herein.

It is preferred that the cloning vector into which the double-stranded cDNA is inserted contains a transcriptional promoter located adjacent to the insertion site, positioned so that the cDNA can be inserted with the 5' end of the sense strand proximal to the promoter. Thus the promoter will be capable of initiating transcription of the cDNA insert. Sequences between the promoter and insert should be minimized, while allowing for the presence of the insertion site itself and the primer/adapter sequences. The promoter is preferably a bacteriophage promoter, most preferably the bacteriophage T7, Sp6 or T3 promoter, for in vitro RNA transcription. Bacteriophage and other viral promoters are preferred due to their specificity and ability to produce large numbers of transcripts. For expression of the cloned cDNA in eukaryotic cells, a promoter appropriate for the particular host cell is used. Suitable promoters in this regard include those from yeast glycolytic genes (Kawasaki, U.S. Pat. No. 4,599,311); fungal genes (published European Patent application EP 272,277); viruses, including SV40 (Subramani et al., *Mol. Cell Biol.* 1:854–864, 1981) and adenovirus (Berkner and Sharp, *Nuc. Acids Res.* 13:841–857, 1985); and mammalian genes, such as the mouse MT-1 gene (palmiter et al., U.S. Pat. No. 4,579,821).

It is preferred that vectors containing a promoter will further contain a terminator located so as to be capable of terminating transcription from the sense strand of the cDNA insert, that is, positioned adjacent to the opposite side of the insertion site from the promoter and in the proper orientation. Suitable transcriptional terminators include those appropriate for termination of the particular RNA polymerase whose promoter is contained within the vector. Terminators may be obtained from genes used as sources of promoters, or from other genes known in the art. Use of a homologous promoter and terminator within a vector is preferred due to specificities of transcriptases. In a preferred embodiment, the vector contains two terminators in tandem, to increase the efficiency of termination.

The vector also contains one or more selectable marker genes, such as a gene conferring ampicillin resistance. Other preferred components of the vector include an intergenic region for M13 or f1 to allow the vector to be packaged as a single stranded DNA. It is also preferred to include a polyadenylation sequence in the vector. This sequence is positioned so as to direct the addition of a poly A tail to mRNA transcribed from the inserted cDNA, i.e., downstream of and adjacent to the cDNA insertion site.

The ligated vector-cDNA complex is inserted into a host cell, generally a bacterial cell such as *E. coli*, for amplification and/or transcription of the cDNA. Use of the electroporation transformation procedure is preferred. Prior to inserting the ligated DNA into the host cells, it is preferred to heat denature any contaminating DNA ligase. Heating the mixture to 65° C. for 10 minutes is sufficient to denature the enzyme. This procedure improves the transformation efficiency as much as 50-fold.

The amplified vector-cDNA may be extracted from the bacterial host cells and inserted into eukaryotic host cells for transcription of the cDNA, if the vector contains an appropriate eukaryotic promoter. In this way, cloned cDNAs may be screened for function in a eukaryotic cell.

mRNA may be transcribed directly from plasmid DNA in constructs containing a bacteriophage promoter. Methods for in vitro transcription are disclosed by, for example, Noma et al. (*Nature* 319: 640-646, 1986) and Melton et al. (*Nuc. Acids Res.* 12: 7035-7056, 1984). Plasmid DNA is prepared from an isolate, a pool of clones, or a cDNA library and transcribed in vitro using a phage RNA polymerase appropriate for the promoter on the vector, for example, bacteriophage T7 RNA polymerase or SP6 polymerase. The RNA may then be used for in vitro translation or for translation in Xenopus oocytes. If the mRNA is to be translated in oocytes, the RNA is preferably synthesized in the presence of capped guanosine nucleotides to provide a capped 5' terminus. It is also preferred that mRNA be polyadenylated if it is to be translated in oocytes. In typical in vitro transcription reaction, 6-12 μg of DNA is combined in a 50.5 μl reaction mixture containing 40 mM Tris pH 8.0, 50 mM NaCl, 8 mM MgCl$_2$, mM spermidine, 0.5 mM each ATP, CTP, GTP and UTP, 1 mM GpppG, 10 μCi α$^{32}$P-ATP, 10 mM dithiothreitol, 25 U ribonuclease inhibitor (RNasin TM, Promega Biotec), 0.1 mg/ml BSA and 70 U T7 RNA polymerase. The mixture is incubated at 37° C. for 75 minutes. To the mixture are added 2 μl ribonuclease inhibitor (RNasin TM, 20 U/μl ), 1 μl 200 mM dithiothreitol and 5 μl DNAse I (200 μg/μl). The mixture is incubated at 37° C. for an additional 15 minutes, and 1 μl is removed for counting β emissions. 100 μl of 20 mM Tris pH 8.5, 200 mM NaCl, 20 mM EDTA is added, and the RNA is extracted twice with phenol-CHCl$_3$ and once with CHCl$_3$. 50 μl of 8 M NH$_4$Ac is added, the RNA is ethanol precipitated and resuspended in H$_2$O. Prior to injection into oocytes, the RNA is centrifuged to remove particulates, lyophilized and resuspended in H$_2$O (treated with diethylpyrocarbonate) at 1 μg/μl. This approach may be utilized to screen a cDNA library by functional analysis. A library is constructed and subdivided into pools. After isolation of plasmid DNA from each pool, RNA is transcribed from the plasmid DNA and injected into oocytes. The translation products from the oocytes are assayed for functional activity, those pools showing biological activity are subdivided, and the process is repeated until a pure clone encoding the protein of interest is obtained.

In a second application, RNA prepared according to the present invention is used for subtraction hybridization. The RNA is biotinylated during synthesis and is hybridized to other nucleic acids (e.g., a cDNA library). Typically, a library of single-stranded DNA derived from a source that produces a protein of interest is hybridized to biotinylated RNA transcribed from a control (negative for the protein of interest) cDNA library. Unhybridized nucleic acids are then separated from the biotinylated hybrids by phenol extraction. Biotinylated hybrids fractionate into the phenol phase and the single stranded, unhybridized nucleic acids are recovered from the aqueous phase and cloned.

In yet another application, radiolabeled RNA probes may be synthesized by transcribing the cloned cDNA in the presence of radioactive nucleotides. RNA prepared in this way may be used as a probe in hybridization experiments to detect complementary sequences.

In those constructs that contain a promoter, mRNA may be transcribed from the cDNA insert in vivo. Vectors containing eukaryotic promoters may be amplified in a bacterial host, then vector DNA is prepared from a single isolate, a pool of clones, or a whole library and transfected into appropriate host cells, for example, mammalian, yeast or other fungal cells. The endogenous RNA polymerase(s) recognize the RNA transcription promoter and terminator(s) of the construct and transcribe the cDNA into mRNA, which is then translated. The host cells are screened for the activity of interest and positive clones are recovered. The cloned cDNA may be transcribed in the bacterial host when the vector contains an appropriate prokaryotic promoter.

The following examples are offered by way of illustration, not by way of limitation.

EXAMPLE 1

Construction of an Expression Vector Containing T7 Transcriptional Terminators

To permit transcription of cloned cDNA without prior endonuclease digestion, bacteriophage T7 transcriptional terminators were added to a cloning vector. The sequence of the putative T7 RNA transcription terminator, which lies between gene and 10 and gene 11 of bacteriophage T7, is disclosed by Dunn and Studier (*J. Molec. Biol.* 166: 477-536, 1983). Four synthetic oligonucleotides were designed from this sequence and ligated into the vector pGEM-1 (obtained from Promega Biotec, Madison, Wis.), a plasmid containing a bacterial origin of replication, ampicillin resistance gene, and the T7 promoter adjacent to a multiple cloning site. 5' terminal phosphates were added to oligonucleotides ZC776 and ZC777 with T4 polynucleotide kinase and ATP, under standard conditions (Maniatis et al. ibid). (The sequences of these and other oligonucleotides referred to herein are shown in the Table.) After the incubation, the kinase was heat killed at 65° C. for 10 min. 25 ng of oligonucleotide ZC775 and 25 ng of oligonucleotide ZC776 were annealed together by incubation at 65° C. for 15 minutes, then allowed to cool to room temperature in 500 ml of water. Oligonucleotides ZC777 and ZC778 were similarly annealed. The annealed oligonucleotides were stored at −20° C. until use. The vector pGEM-1 was digested with Pst I and Hind III, and the vector DNA was purified away from the small oligonucleotides by agarose gel electrophoresis. The synthetic oligonucleotide T7 terminator was then cloned into pGEM-1. Twenty-five nanograms of vector plus an equal molar amount of each of the oligonucleotides ZC775 through ZC778 were combined in a 10 μl reaction mix. After ligation overnight at 14° C., the DNA was transformed into competent *E. coli* JM83 cells, and the transformed cells were plated on LB-ampicillin plates. Plating out 1/10th of the transformation reaction produced 45 colonies. Twenty-four of these colonies were picked into 5 ml LB-ampicillin for overnight cultures. Mini-prep plasmid DNA was prepared from these overnight cultures by the alkaline lysis procedure (Birnbaum and Doly, *Nuc. Acids Res.* 7: 1513-1523, 1979). A portion of the DNA from these samples was cut with Pst I and Hind III and analyzed on a 4% polyacrylamide gel to identify clones that released an 80 bp Pst I-Hind III fragment. Other diagnostic cuts, such as Eco RI and Not I, were also made. One of the isolates, which was named pGEMT (FIG. 1), was inoculated into a 500-ml culture of LB-ampicillin and grown overnight. Plasmid DNA was prepared from this culture by the alkaline lysis procedure and was purified twice by cesium chloride gradient centrifugation.

TABLE

| Oligonucleotide | Sequence (5'-3') |
|---|---|
| ZC525 | GGAATTCT |
| ZC526 | GATCAGAATTCC |
| ZC553 | AATTGATAGCGGCCGCTTACTGCA |
| ZC554 | GTAAGCGGCCGCTATC |
| ZC775 | GCTAGCATAACCCCTTGGGGCCTCTAAACGGGTCT |
| ZC776 | CTCAAGACCCGTTTAGAGGCCCCAAGGGGTTATGCTAGCTGCA |
| ZC777 | TGAGGGGTTTTTTGCTGAAAGGAGGAACTATGCGGCCGCA |
| ZC778 | AGCTTGCGGCCGCATAGTTCCTCCTTTCAGCAAAAAACCC |
| ZC1750 | AGGGAGACCGGAATTCCCCCCCCCC |
| ZC1751 | AATTCTGTGCTCTGTCAAG |
| ZC1752 | GATCCTTGACAGAGCACAG |
| ZC1753 | GACAGAGCACAGAATTTTTTTTTTTTTTT |
| ZC1773 | AATTAGGGAGACCGGAATTCTGTGCTCTGTCAA |
| ZC1774 | AATTTTGACAGAGCACAGAATTCCGGTCTCCCT |
| ZC1775 | CGCTCAGCTGGAATTTTGACAGAGCA |
| ZC2013 | TACCGAGCTCGAATTTTGACAGAGCA |
| ZC2063 | GATCCAAACTAGTAAAAGAGCT |
| ZC2064 | CTTTACTAGTTTG |
| ZC2065 | AATTTATGCGGCCGCTATCATG |
| ZC2066 | ATAGCGGCCGCATA |
| ZC2067 | TATGCGGCCGCTATAGCT |
| ZC2068 | ATAGCGGCCGCATACATG |
| ZC2090 | CTAGATGATTGC |
| ZC2110 | GGCCGCAATCAT |
| ZC2185 | ATAGCGGCCGCATA |
| ZC2186 | GATCTATGCGGCCGCTATAGCT |
| ZC2187 | GATCATAGCGGCCGCATA |
| ZC2188 | AATTTATGCGGCCGCTAT |

To test the effectiveness of the terminator, pGEMT, linearized with Not I or unlinearized, was transcribed with T7 RNA polymerase using a modification of the procedure described by Melton et al. (*Nucl. Acids Res.* 12: 7035-7056, 1984). The products were run on a 10% polyacrylamide gel. With the Not I linearized template, about 20% of the RNA terminated at the terminator and 80% terminated at the end of the template (Not I site). With the unlinearized template, there was very little termination in the terminator region.

Due to the limited effectiveness of the synthetic terminator, a plasmid containing the native T7 terminator was constructed. Plasmid pAR2529, which contains the native T7 terminator (Rosenberg et al., *Gene* 56: 125-135, 1987), was tested in the transcription assay essentially as described above. RNA was transcribed from a Bgl II linearized plasmid or from an unlinearized plasmid in the presence of alpha $^{32}$P-UTP. The products were analyzed on a 10% polyacrylamide gel and subjected to autoradiography. Bands from the gel were excised and counted in a scintillation counter. Comparing the number of counts in the band that represented the RNA that terminated at the T7 transcription terminator with the counts in the band that represented the runoff RNA, it appeared that the terminator was about 70% effective in terminating transcription.

To add the natural terminator to pGEMT, the plasmid was digested with Bam HI and the plasmid pAR2529 was digested with Bam HI and Bgl II (FIG. 1). The Bam HI-Bgl II terminator fragment from pAR2529 was purified by agarose gel electrophoresis. The terminator fragment was ligated to Bam HI digested pGEMT, and the DNA was transformed into competent *E. coli* LM1035 cells. Colonies that grew up on LB-ampicillin plates were inoculated into 5 ml cultures for overnight growth. Plasmid DNA was prepared by the alkaline lysis mini-prep procedure. Clones were screened for proper terminator orientation by Bam HI-Sal I digestion and electrophoresis on an 8% polyacrylamide gel. A clone that contained the terminator in the correct orientation, as evidenced by the presence of a 130 bp Bam HI-Sal I fragment, was chosen and named pGEMTT (FIG. 1).

To determine the effectiveness of the terminators, chloramphenicol acetyl transferase (CAT) cDNA and granulocyte-macrophage colony stimulating factor (GM-CSF) cDNA were separately cloned into pGEMTT. DNA that was either unlinearized or linearized with Not I was transcribed with T7 RNA polymerase, and the products were run on a glyoxal agarose gel. The gel was dried and exposed to photographic film. About 60% of the RNA transcribed from the Not I-linearized CAT plasmid terminated at the native T7 terminator. The results from the unlinearized CAT plasmid indicated that the native terminator is fairly effective in terminating RNA transcription and that the synthetic terminator also is somewhat effective in termination. Similar patterns were observed for transcription of the GM-CSF plasmids. These experiments demonstrated that plasmids containing T7 transcription terminators are useful as vectors for the construction of expression cDNA libraries in which T7 DNA polymerase is used to transcribe the cloned cDNA.

EXAMPLE 2

The Addition of the M13 Intergenic Region to pGEMTT

To allow pGEMTT to be packaged as single-stranded DNA in the presence of M13 phage proteins, the M13 intergenic region from pUC382 (similar to pUC118 and 119 as disclosed by Vieira and Messing, *Methods Enzymol.* 153:3-11, 1987) was added to pGEMTT (FIG. 1). pGEMTT was digested with Fsp I and Nar I, and the fragment containing the T7 promoter and transcription terminator was purified. pUC382 was digested with Fsp I and Nar I, and the fragment encoding the ampicillin resistance gene and the M13 intergenic region was gel purified. These fragments were then ligated together in the presence of T4 DNA ligase. The ligated DNA was transformed into competent *E. coli* LM1035 cells. After overnight growth on LB-ampicillin plates, 12 colonies were picked into 5 ml of LB-ampicillin and grown overnight. Plasmid DNA was prepared by the alkaline lysis mini-prep method. The clones were screened by digesting with Ava I. The appropriate construction gave two bands, one of 2430 bp and another of 709 bp. One such isolate was chosen and named pVEG.

Plasmid pVEG was further characterized to show that infection with M13 resulted in encapsulation of the single-stranded pVEG and that the single-stranded DNA that was encapsulated would be the complement of RNA synthesized from the T7 promoter of this plasmid. This was accomplished by probing dot blots of single-stranded pVEG with $^{32}$P-labeled synthetic oligonucleotides ZC777 and ZC778 from the synthetic terminator. The desired isolate gave a strong hybridization signed with ZC777, whereas ZC778 did not give a hybridization signal. In addition, this demonstrated that only the appropriate strand of pVEG was being packaged by the M13 phage proteins.

EXAMPLE 3

Modification of pVEG for Directional Cloning

Figure 2:
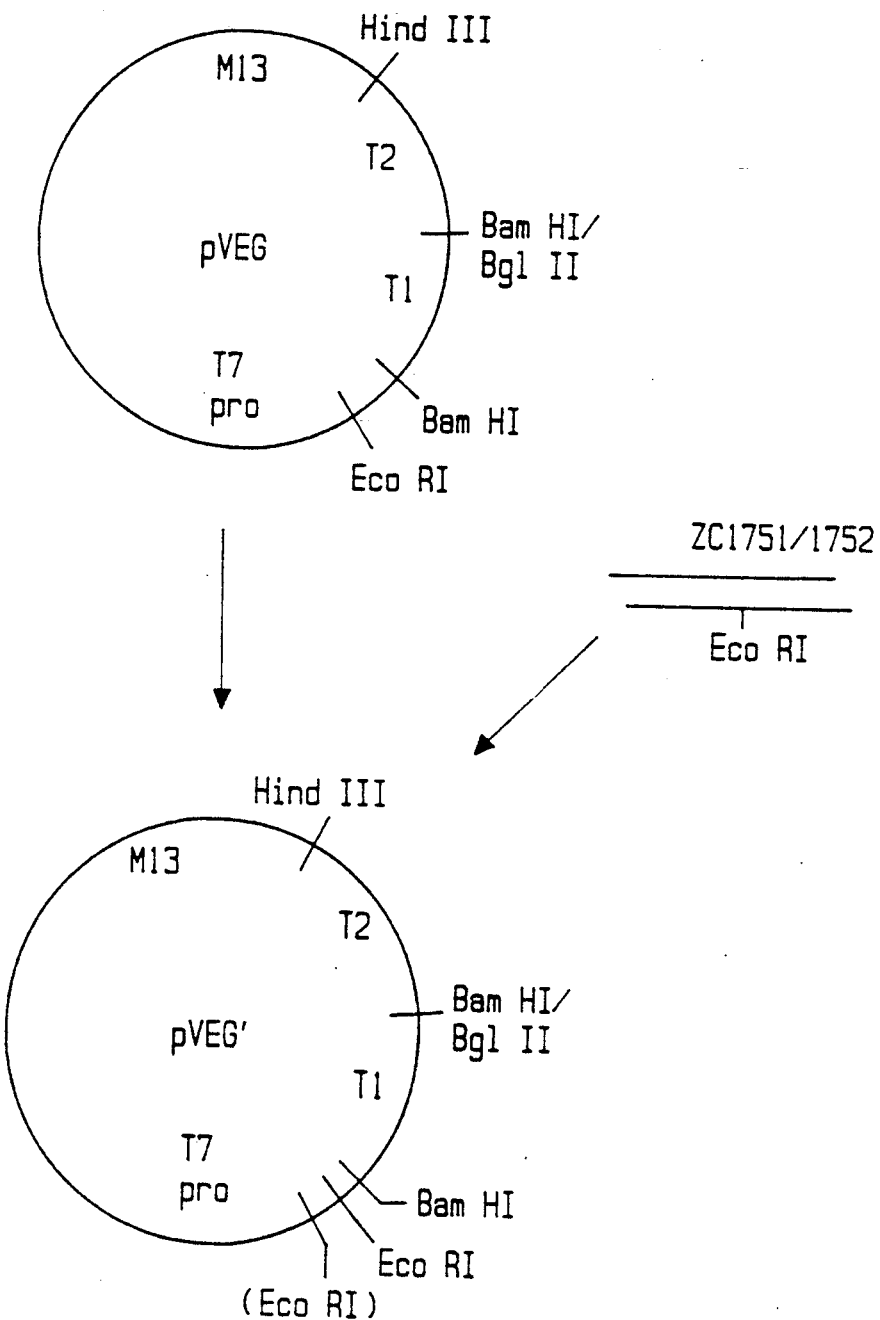
FIG. 2 illustrates the construction of a directional cloning vector containing the M13 intergenic region. Parentheses indicate a restriction site destroyed in vector construction.

To make pVEG useful for directional cloning, synthetic oligonucleotides (the prime sequence) were added between the Bam HI and Eco RI sites of pVEG (FIG. 2). pVEG was digested with Bam HI and Eco RI and the vector fragment was gel purified. 96 nanograms each of oligonucleotides ZC1751 and ZC1752 were annealed in 4.5 µl of 10 mM Tris pH 7.5, 20 mM MgCl$_2$ and 10 mM NaCl at 65° C. for 20 minutes, then the mixture was cooled to room temperature over a period of 30 minutes. The annealed oligonucleotides were ligated to the pVEG vector fragment with T4 DNA ligase and then transformed into competent *E. coli* LM 1035 cells. After growing overnight to develop the colonies, a filter lift was taken of the colonies on the agar plate. The filter was probed with $^{32}$P-labeled oligonucleotide ZC1751. All of the colonies were positive. Mini-prep DNA was prepared from cultures grown from 12 of the colonies. The mini-prep DNA was screened by digestion with Sst I to verify the absence of the Sst I site between the Eco RI and Bam HI sites of pVEG. All 12 of the mini-prep DNAs were negative for Sst I digestion. One of these 12 isolates was chosen and named pVEG'.

EXAMPLE 4

The Addition of a Polyadenylation Sequence to pVEG

Figure 3:
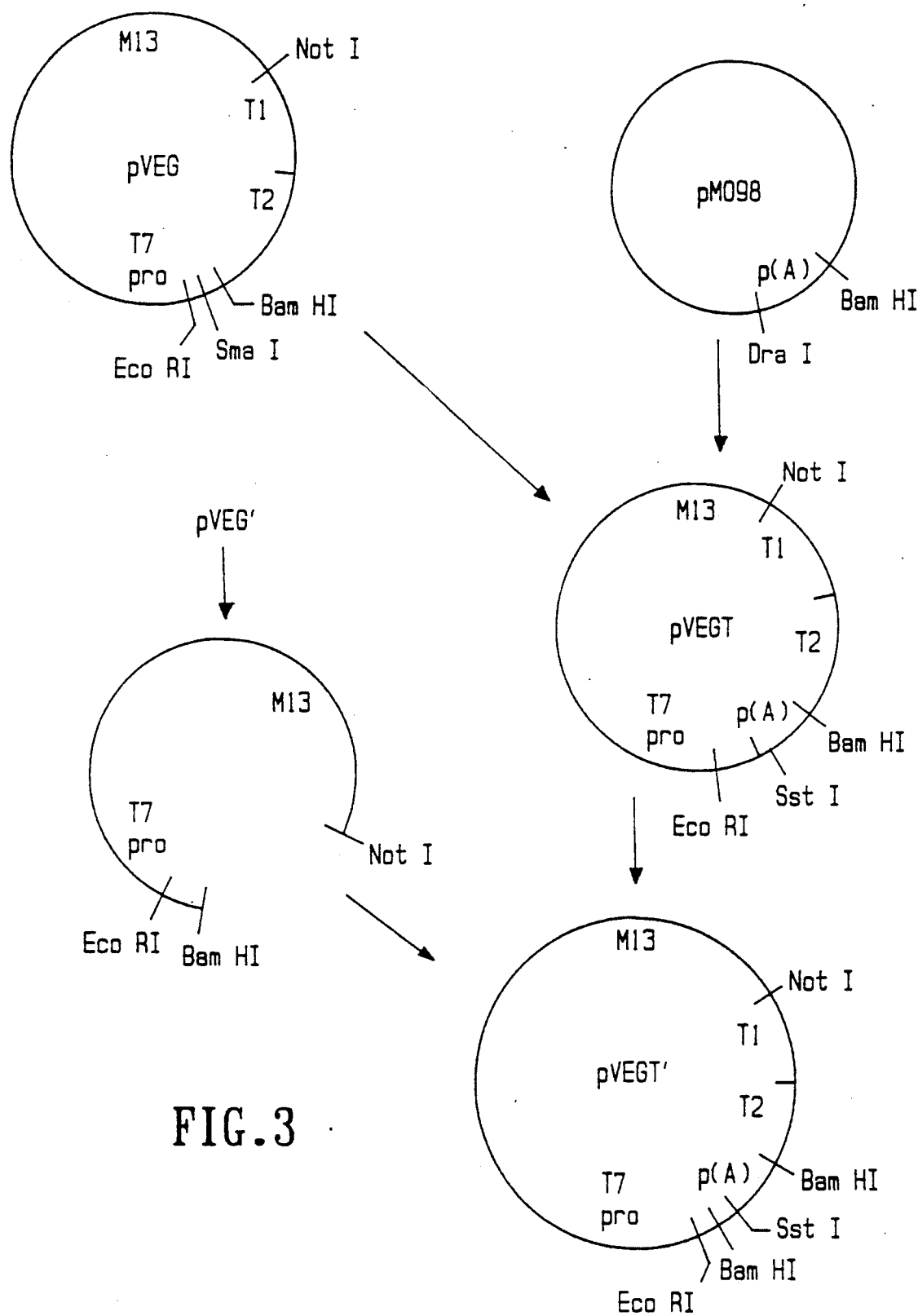
FIG. 3 illustrates the construction of a directional cloning vector containing an Aspergillus niger polyadenylation sequence (designated as p(A)) adjacent to the cloning site.

A polyadenylation sequence was derived from a clone of *Aspergillus niger* alcohol dehydrogenase cDNA. As shown in FIG. 3, plasmid pM098 (disclosed in published European patent application EP 272,277 and deposited with American Type Culture Collection under accession number 53428) was digested with Dra I and Bam HI, and the approximately 150 bp poly A fragment was purified by agarose gel electrophoresis. This fragment contained mostly poly A sequence with very little flanking cDNA. To clone the poly A cDNA fragment into pVEG, pVEG was digested with Bam HI and Sma I, and the 3.4 kb vector fragment was gel purified. The vector and poly A fragments were ligated together with T4 DNA ligase to produce vector pVEGT (FIG. 3).

The bacterial chloramphenicol transferase (CAT) gene (Gorman et al., *Mol. Cell. Biol.* 2:1044–1051, 1982) was cloned into the Eco RI site of pVEGT to test the effect of the poly A sequence on the translation of this reporter sequence in oocytes. RNA was transcribed in vitro from this construct and a similar construct lacking the poly A sequence and was translated in oocytes according to standard procedures. Various dilutions of the ground up oocytes were assayed for CAT activity. This assay revealed that the poly A+RNA encoded at least 40 times more CAT activity than RNA transcribed from a construction without poly A.

EXAMPLE 5

Addition of a Directional Cloning Site to pVEGT

In order to use the pVEGT plasmid in directional cloning, the directional cloning site (the "prime" sequence) was added to this plasmid (FIG. 3). To accomplish this, pVEGT was digested with Not I and Sst I, and the 370 bp fragment containing the poly A sequence and the two T7 transcriptional terminators was purified by agarose gel electrophoresis. pVEG' was digested with Not I and Bam HI, and the 3.2 kb vector fragment was gel-purified. Two oligonucleotides that would form a Bam HI-Sst I adapter were synthesized. The two oligonucleotides (ZC2063 and ZC2064) were individually kinased and annealed, and the vector, the poly A-terminator fragment, and the oligonucleotide adapter were ligated with T4 DNA ligase. This produced a vector called pVEGT, (FIG. 3), which contains a T7 RNA transcription promoter, an Eco RI cloning site flanked by the prime sequence, a poly A stretch, and two T7 RNA polymerase terminators.

EXAMPLE 6

Directional Cloning Vector For Mammalian Cell Expression

The mammalian expression vector pVAPDBam8 (FIG. 4), an adenovirus-based vector, was the starting material for the construction of a mammalian cell vector containing the directional cloning features. The important elements of this vector are an adenovirus origin of replication, an SV40 enhancer, the adenovirus 2 major late promoter and tripartite leader sequence, a pair of RNA splice sites, a cloning site, and a poly A addition sequence. As will be appreciated by those familiar with the art, these elements may be obtained from a variety of sources, and the particular starting materials and manipulations described herein were chosen for convenience. To facilitate the subcloning of Eco RI cloned cDNAs into this expression vector, an Eco RI cloning site was added to pVAPDBam8.

Figure 4:
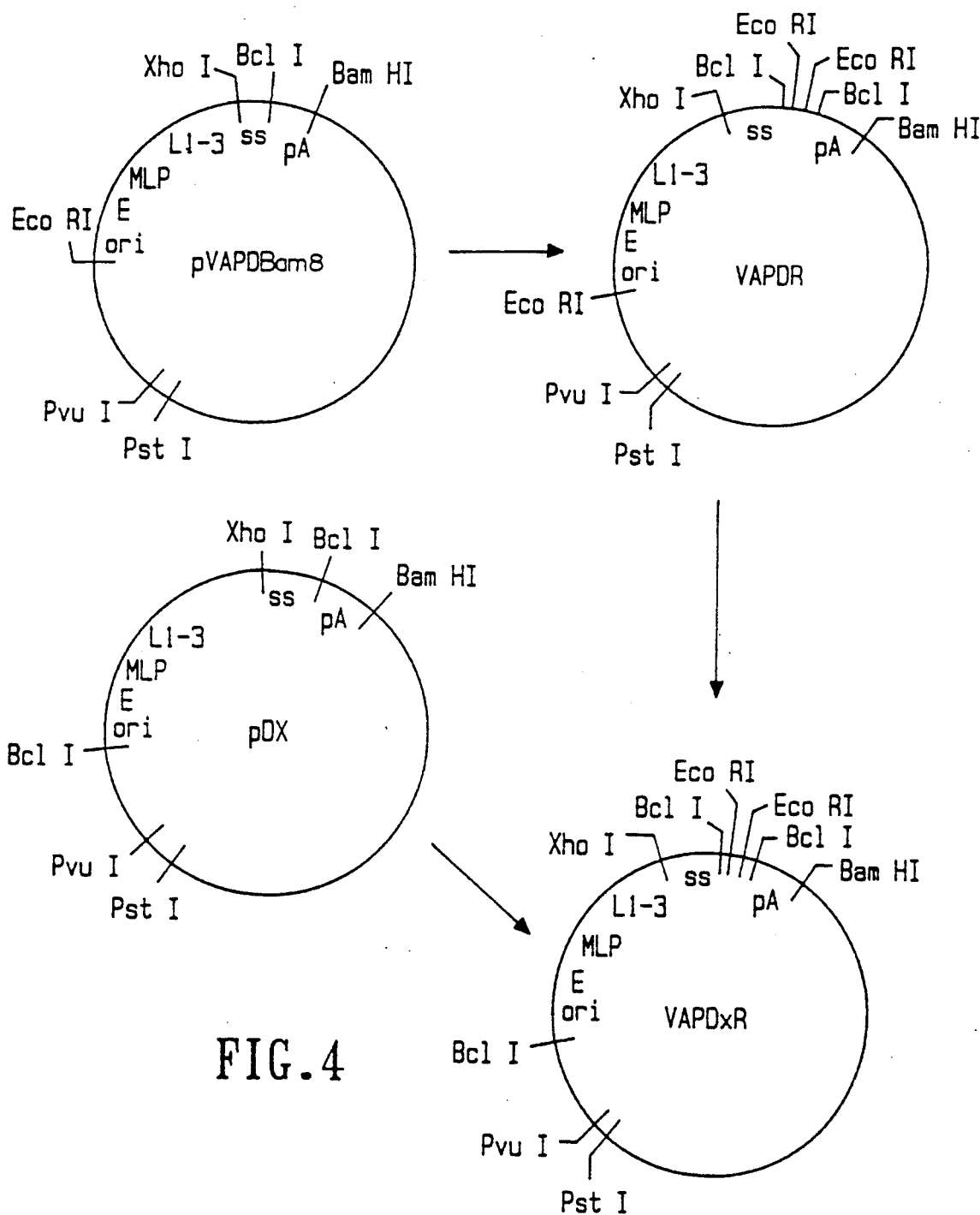
FIGS. 4 and 5 illustrate the construction of a directional cloning vector that can be used for expressing cloned cDNA in mammalian cells. Symbols used include ori, the adenovirus 5 0-1 map unit sequence; E, SV40 enhancer; MLP, the adenovirus 2 major late promoter; L1-3, the adenovirus 2 tripartite leader; SS, a set of RNA splice sites; and pA, the SV40 polyadenylation sequence.

The vector was first modified so that the prime sequence could be inserted at the Bcl I site. To prepare pVAPDBam8 for digestion with Bcl I, which requires the absence of methylated sites within the recognition sequence, the plasmid was transformed into *E. coli* DH1 (a modification plus and restriction minus strain) and subsequently transformed into *E. coli* GM-48, (modification minus and restriction minus). The resulting plasmid, pVAPDBam8-1, was digested with Bcl I. An adapter formed by two kinased oligonucleotides, ZC525 and ZC526, was ligated with the Bcl I-digested vector. To make this construction two adapters had to blunt-end ligate, then the double adapter had to ligate into the Bcl I cloning site, resulting in a vector having two Eco RI sites flanked by Bcl I sites. This vector was named VAPDR (FIG. 4). To remove the other Eco RI site near the viral origin of replication of this vector, VAPDR was digested with Xho I and Pvu I, and the 3.2 kb fragment, containing the splice sites and polyadenylation sequence, was gel purified. From the similar vector pDX (disclosed in published European patent application EP 276,846 and shown in FIG. 4). a 1.7 kb Xho I-Pvu I fragment, containing the adenovirus origin of replication, SV40 enhancer and adenovirus major late promoter, was gel purified. These two fragments were ligated together with T4 DNA ligase to produce the vector VAPDxR (FIG. 4).

Figure 5:
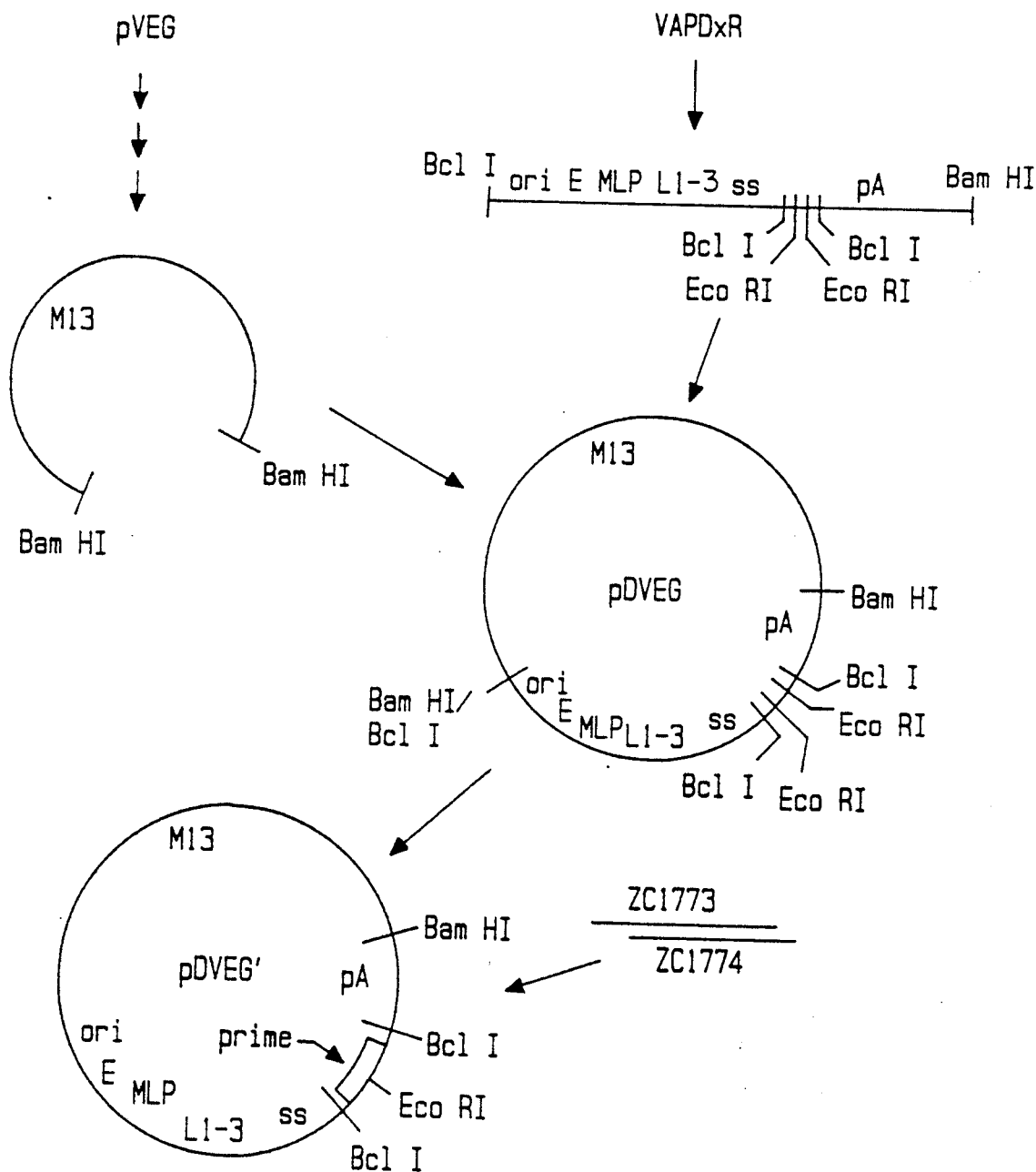

The M13 intergenic region was then added to VAPDxR. Plasmid pVEG was digested with Pvu II and Nar I, blunted with T4 DNA polymerase, then Bam HI linkers were added with T4 DNA ligase. The ligation products were digested with Bam HI, and the DNA fragment was gel purified (FIG. 5). VAPDxR was digested to completion with Bam HI and partially digested with Bcl I. The Bcl I-Bam HI fragment containing the adenovirus expression unit was gel purified. The fragments from pVEG and VAPDxR were ligated and transformed into competent E. coli LM 1035 cells. The construction was screened for correct orientation of the intergenic region. The orientation desired would provide single-stranded DNA of anti-sense polarity in regard to RNA synthesized by the major late promoter. A construct having this configuration was named pDVEG.

To add the prime sequence to pDVEG, this plasmid was digested with Eco RI (FIG. 5). The prime sequence, constructed by annealing oligonucleotides ZC1773 and ZC1774, Was ligated to the Eco RI-digested vector. The ligated DNA was electroporated into DH5αF' ™ cells (obtained from Bethesda Research Laboratories), and the cells were plated. Colony blots were obtained and probed with labeled ZC1773 and ZC1774. Plasmid DNA was prepared from positive colonies and electroporated into XL-I blue cells (obtained from Stratagene), which contain a tetracycline resistant F' required for M13 infection. The transformed cells were plated on LB-tetracycline and ampicillin plates. Plasmid DNA was prepared from colonies that were resistent to both tetracycline and ampicillin. The region around the Eco RI site was sequenced by double-stranded dideoxy-chain termination DNA sequence analysis. A construct with the correct orientation of the prime sequence was selected and named pDVEG'.

EXAMPLE 7

Directional Cloning Vector for Yeast Expression

Figure 6:
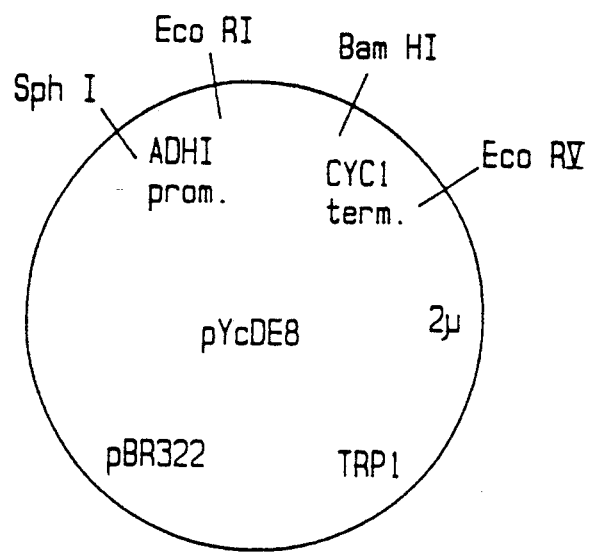
FIG. 6 illustrates the construction of a directional cloning vector for use in yeast.
Figure 6:
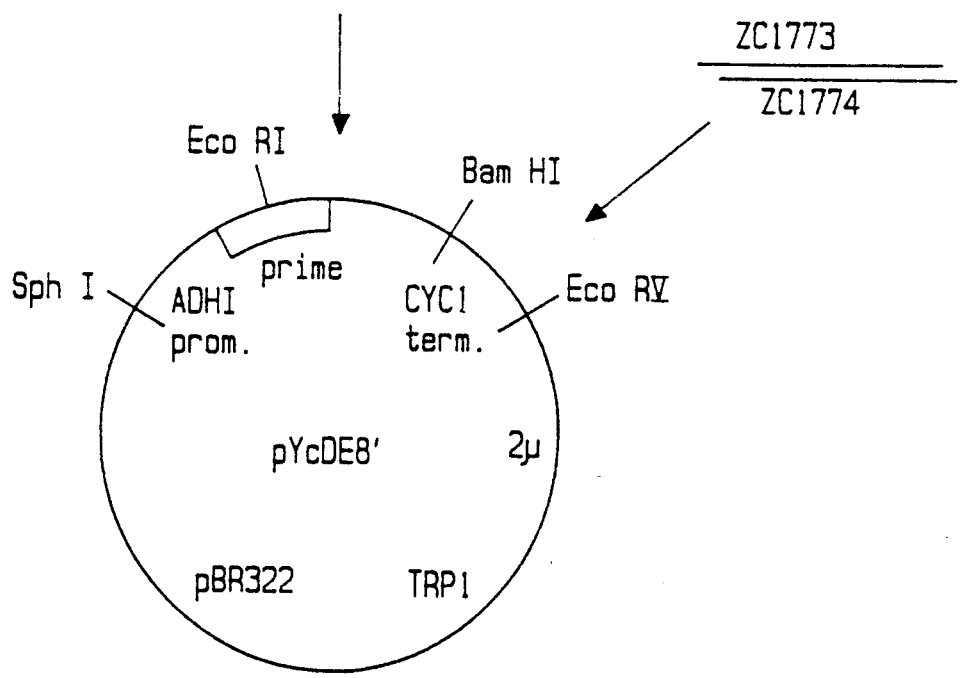

To add the prime sequence to the yeast expression vector pYcDE8 (McKnight et al., EMBO J. 4: 2093-2099, 1985), this plasmid was digested with Eco RI and ligated with a prime sequence constructed from oligonucleotides ZC1773 and ZC1774. After electroporation into cells and plating on LB-ampicillin plates, a colony lift was taken and probed with radiolabeled ZC2013. ZC2013 hybridizes to the desired isolate by virtue of the fact that it is complementary to part of the ZC1773 sequence and part of the pYcDE8 sequence. A positive isolate was chosen and named pYcDE8' (FIG. 6).

EXAMPLE 8

Construction of a λ Cloning Vector Containing the Plasmid pYcDE8'

Figure 7:
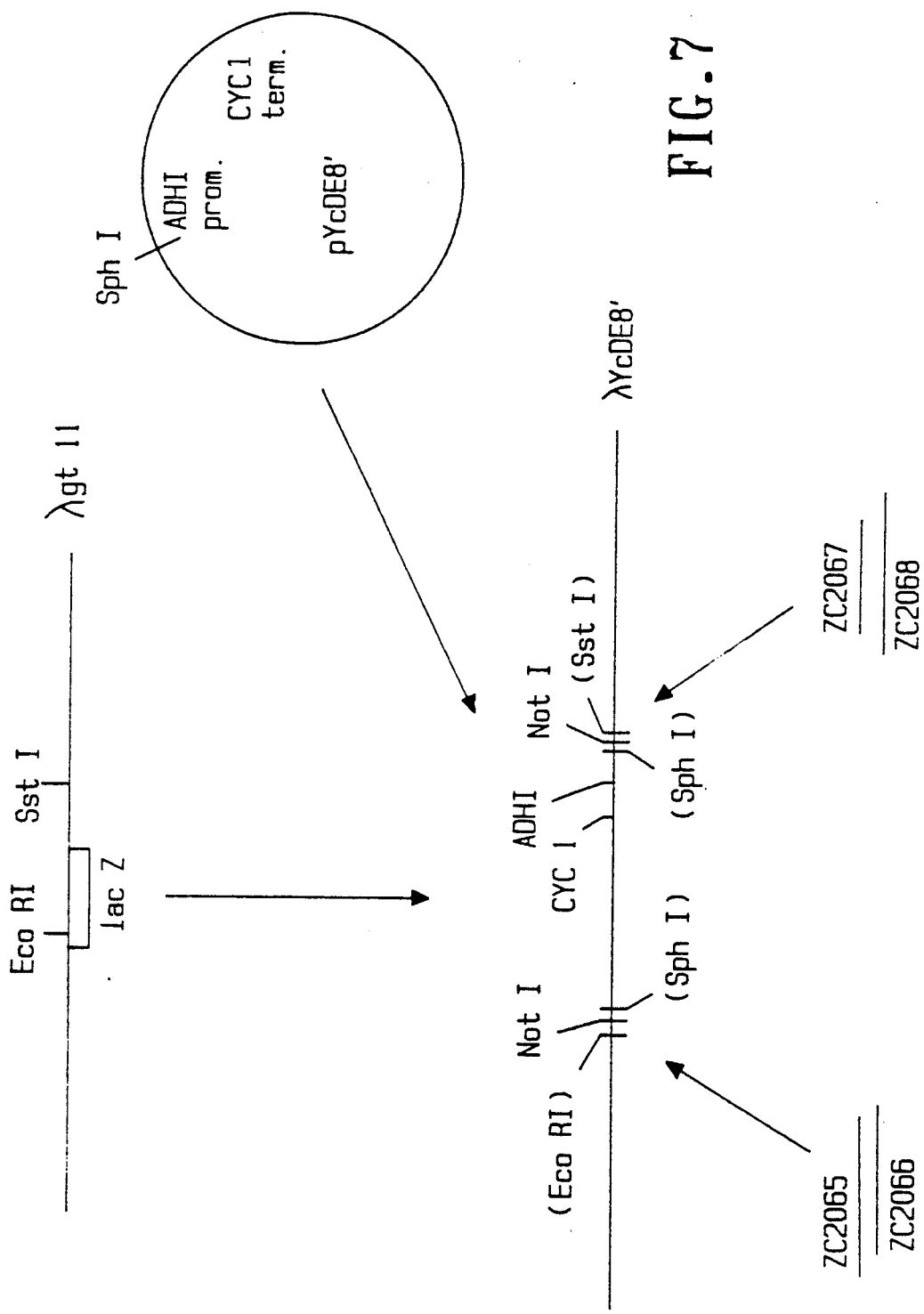
FIG. 7 illustrates the insertion of plasmid pYcDE8' into λgt11.

The plasmid pYcDE8' was inserted into a λ vector. As shown in FIG. 7, λgtll was digested with Eco RI and Sst I and the phosphates on the termini of the DNA were removed by treatment with calf alkaline phosphatase. Digestion of λgtll with Eco RI and Sst I removes about 5.49 kb of DNA so that when pYcDE8' is inserted into this λ vector, the exclusion size of the hybrid vector is not greatly changed from that of native λgtll. Two adapters were designed that would link the Sph I sites on pYcDE8' with the Eco RI and Sst I sites on the λ arms. A Not I site is contained within each of the adapters. Ligation of the adapters to the λ arms destroys the original Sph I, Eco RI and Sst I sites. As shown in FIG. 7, oligonucleotides ZC2065 and ZC2068 were kinased and annealed to their complementary oligonucleotides, ZC2066 and ZC2067, respectively. pYcDE8' was digested at its unique Sph I site. The linearized pYcDE8', the λ arms and the adapters were mixed together and ligated with T4 DNA ligase. The construction was packaged with lambda packaging mix and plated on E. coli Y1088 host cells. An isolate was obtained by plaque purification using random-primed pYcDE8' as a probe.

EXAMPLE 9

Adding the Prime Sequence to λgt11

To utilize directional cloning in λgt11 the prime sequence was added to the phage vector. λgt11 was digested with Eco RI and ligated with the prime sequence, which was constructed by annealing oligonucleotides ZC1773 and ZC1774. Oligonucleotide ZC1775, which was designed to overlap the prime sequence and a part of the λgt11 sequences, was used as a probe to plaque purify an isolate with the proper orientation of the prime sequence. The insertion of the prime sequence into the Eco RI site of λgt11 inactivates the original Eco RI site, but provides a new Eco RI site within the prime sequence.

EXAMPLE 10

Construction of a λ Vector Containing the pVEGT' Plasmid

Figure 8:
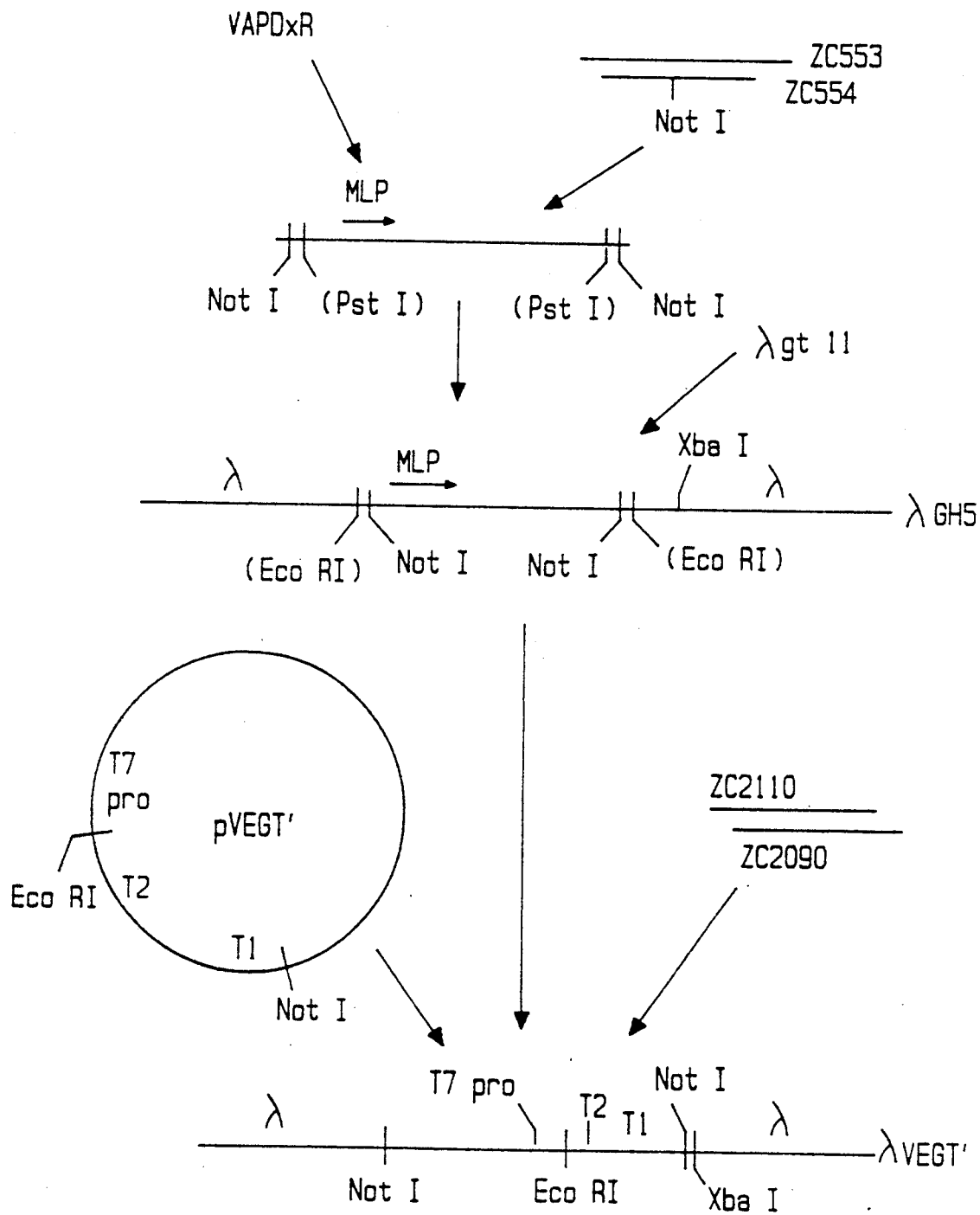
FIG. 8 illustrates the insertion of plasmid pVEGT' into λgt11.

To combine the in vitro RNA transcription feature of plasmid pVEGT' with the λ phage system of cDNA library construction, pVEGT' was inserted into a λ vector (FIG. 8). pVAPDxR was digested with Pst I, and the 3.8 kb fragment containing the mammalian expression unit was gel purified. Oligonucleotide ZC554 was kinased and hybridized to oligonucleotide ZC553. The resulting linker, which contains a Not I site flanked by Eco RI and Pst I sticky ends, was ligated to the pVAPDxR fragment, and the resulting construct was gel purified. λgt11 was digested with Eco RI. The gel purified pVADPxR-linker construct and the Eco RI λ arms were ligated with T4 DNA ligase. This construction was packaged and plated. The desired isolate was plaque purified using radiolabeled pVAPDxR as the probe and named λGH5. λGH5 was digested with Not I and Xba I, and the λ arms were gel purified. pVEGT' was digested with Not I. The λ arms, linearized pVEGT', and an Xba I -Not I adaptor, consisting of oligonucleotides ZC2110 and ZC2090, were ligated with T4 DNA ligase. The desired isolate was plaque purified using labeled pVEGT' as a probe and was designated λVEGT'.

EXAMPLE 11

Inserting pDVEG' into a λ cloning vector

Figure 9:
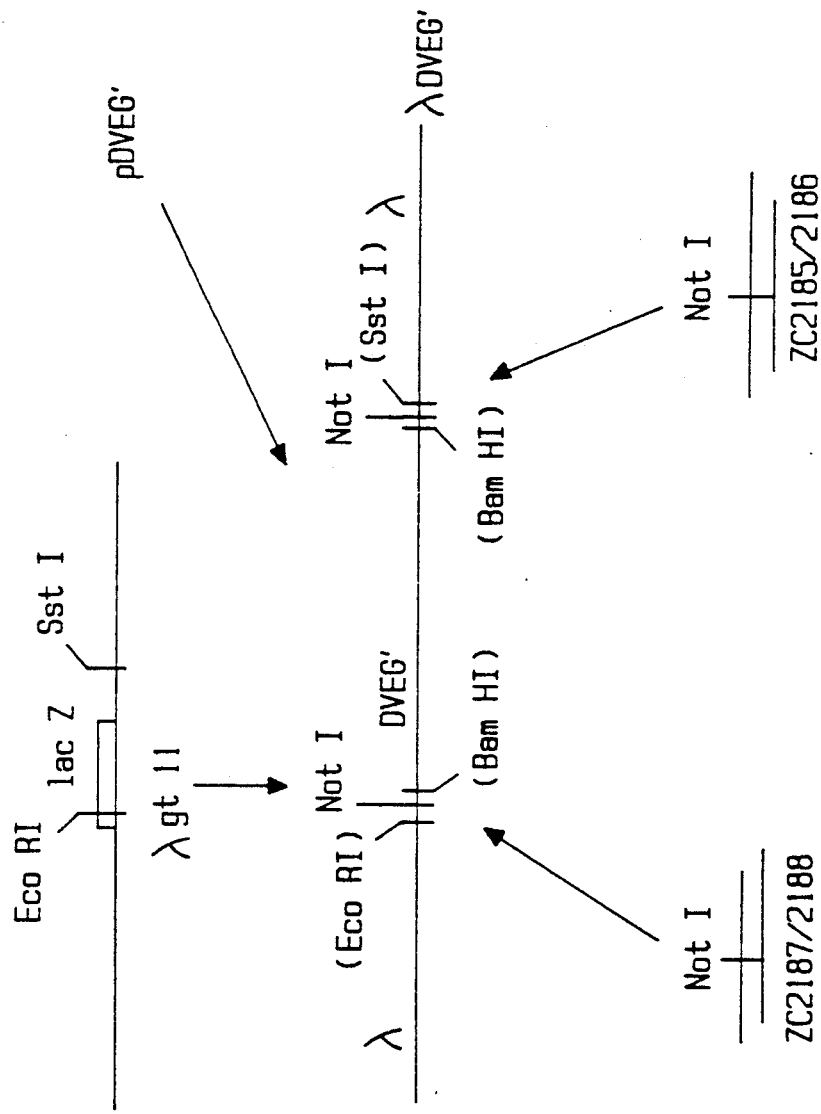
FIG. 9 illustrates the insertion of plasmid pDVEG' into λgt11.

To utilize the plasmid pDVEG' in the λ cloning system, pDVEG' was inserted into a λ vector. λgt11 was digested with Eco RI and Sst I, and the terminal phosphates were removed with calf alkaline phosphatase (CAP) (FIG. 9). Oligonucleotides ZC2188 and ZC2185 were kinased and annealed to oligonucleotides ZC2187 and ZC2186, respectively. These oligonucleotides form Eco RI - Bam HI and Sst I -Bam HI adapters containing Not I sites. pDVEG' was digested with Bam HI. The linearized vector, the adaptors, and the λ arms were ligated together with T4 DNA ligase. The construction was packaged with λ packaging mix and plated. The desired isolate was plaque purified using labeled pDVEG' as a probe. This construction was named λDVEG'.

EXAMPLE 12

Directional Cloning of cDNA

A. First Strand cDNA Synthesis

5 μg of *Humicola inbulans* poly (A)+RNA was heat denatured at 65° C. for 3 minutes and reverse transcribed in 50 μl of 50 mM Tris-HCl pH 8.3, 75 mM KCl, 10 mM DTT, 3 mM MgCl$_2$, 500 μM dXTP, 0.4 μCi/μl alpha $^{32}$P dATP, containing 20 pg/μl of oligonucleotide primer ZC1753 and 20 U/μl MMLV reverse transcriptase (obtained from Bethesda Research Laboratories). The reaction was incubated for 1 hour at 37° C. 50 μl of 20 mM Tris-HCl pH 8.3, 20 mM EDTA, 200 mM NaCl was added. After mixing, 2μl of the solution was TCA precipitated and 1 μl was counted directly to determine total radioactivity and total TCA-precipitable counts in the reaction. The rest of the reaction mixture was twice -phenol-chloroform extracted. 30 μl of 8 M NH$_4$Ac and 300 μl of ethanol were added. After mixing and chilling, the DNA was collected by centrifugation. The pellet was washed with ethanol and resuspended in 50 μl of 50 mM KOH, 0.1 mM EDTA. The RNA was alkaline hydrolyzed at 65° C. for 15 min. The synthesis yielded 1.24 μg of cDNA or a 25% conversion of RNA into cDNA.

The cDNA was chromatographed on a 1 ml Sepharose CL-6B column, poured in a 1 ml disposable pipet, in 50 mM KOH, 0.1 mM EDTA. (The column was washed with 50 column volumes of buffer prior to use.) The cDNA in the void volume was collected and ethanol precipitated after adding 5 μg of carrier oyster glycogen. 385 ng of cDNA was recovered from the pooled void volume peak fractions.

B. Tailing cDNA

The cDNA was tailed with dGs using terminal deoxynucleotidyl transferase (TdT) in 12.5 μl of 100 mM potassium cacodylate, pH 7.2, 2 mM CoCl$_2$, 0.2 mM DTT, 100 μM dGTP, 1 mg/ml BSA, and 3.8 U/μl TdT (obtained from Collaborative Research). The reaction was incubated for 3 minutes at 15° C. 80 μl of 20 mM Tris-HCl pH 8.3, 20 mM EDTA, 200 mM NaCl was added, and the solution was twice phenol-chloroform extracted. The DNA was ethanol precipitated, centrifuged, rinsed with ethanol, and dried.

C. Second Strand cDNA Synthesis

Second strand cDNA synthesis was performed in 50 μl of 10 mM Tris-HCl, pH 8.3 (at room temperature), 50 mM KCl, 1.5 mM MgCl$_2$, 0.01 mg/ml gelatin, 10 ng/μl oligonucleotide primer ZC1750, 200 μM dXTP, and 0.1 U/μl Taq I DNA polymerase (Perkin Elmer Cetus). The mixture was incubated at 94° C. for 3 minutes, 50° C. for 3 minutes, and 72° C. for 12 minutes. 50 μl of 20 mM Tris-HCl, pH 8.3, 20 mM EDTA, 200 mM NaCl was added, and the solution was twice phenol-chloroform extracted. The DNA was ethanol precipitated, centrifuged, and rinsed with ethanol.

The cDNA was chromatographed on a 1 ml Sepharose CL-2B column. poured in a 1 ml disposable pipet. in 10 mM Tris-HCl pH 7.4, 150 mM NaCl, 0.1 mM EDTA. (The column was washed with 50 column volumes of buffer before use.) The void volume fractions containing the DNA were pooled and the DNA was ethanol precipitated, rinsed, and dried.

D. Exposing Single Stranded Ends of the cDNA

To expose single stranded ends of the cDNA, the cDNA was treated with T4 DNA polymerase in the presence of dATP in a 10 μl reaction with the following reaction conditions: 33 mM Tris-acetate pH 7.9, 67 mM KAc, 10 mM MgAc, 0.1 mg/ml gelatin, 200 μM dATP, 5 mM DTT, and 0.1 U/μl T4 DNA polymerase (Boehringer-Mannheim). (These conditions are optimal for a few hundred ng to 1 μg of cDNA.) The reaction was incubated at 15° C. for 1 hour. After addition of 90 μl of 20 mM Tris-HCl pH 8.3, 20 mM EDTA, and 200 mM NaCl, the solution was twice phenol-chloroform extracted, and the DNA was ethanol precipitated.

E. Preparation of the Plasmid pYcDE8' to Accept cDNA pYcDE8' was digested with Eco RI under conditions specified by the enzyme manufacturer. Single-stranded ends of the vector were exposed by treatment with T4 DNA polymerase in the presence of dTTP. 50 μg of Eco RI-linearized plasmid was exonucleased with T4 DNA polymerase in a 500 μl reaction, using conditions described in Section D (above), except for the substitution of 200 μM dTTP for dATP. After phenol-chloroform extraction and ethanol precipitation, the DNA was resuspended in water at 0.5 μg/μl. This is exonucleased vector was called pYcDE8' -cb.

F. Hybridization and Ligation of Humicola cDNA to pYcDE8' -cb 100 ng of Humicola cDNA and 400 ng of pYcDE8'-cb were annealed and ligated in a 100 μl reaction under the following conditions: 50 mM Tris-HCl pH 7.8, 5 mM MgCl $_2$, 100 ng/μl oyster glycogen, 500 μM ATP, 10 mM DTT, 0.005 Weiss U/μl T4 DNA ligase (Boehringer-Mannheim), and 0.5 U/μl T4 polynucleotide kinase (Boehringer-Mannheim). The reaction was incubated at 37° C. for 3 hours. The kinase and ligase were heat killed by incubation at 65° C. for 10 min. The DNA was electroporated using a BioRad Gene Pulser and Pulse Controller into *E. coli* DH5αF' ™ cells to establish a library of 3.1×10$^6$ isolates with a 1 % background. The cloning efficiency was 6.6×10$^6$ clones per μg of cloning vector or 2.6×10$^7$ clones per μg of cDNA.

The above-described procedure was also used to directionally clone cDNA into the other prime plasmid vectors pVEGT' and pDVEG'.

EXAMPLE 13

Directional Cloning of cDNA into λ Prime Vectors

To demonstrate the utility of the μ prime vectors in directional cloning, they were utilized to establish cDNA libraries. A globin cDNA was transcribed from globin mRNA (obtained from Bethesda Research Laboratoris). cDNA was prepared from HepG2 cells as described in U.S. Pat. No. 4,784,950. These cDNAs were then directionally cloned in λVEGT'.

The vector λVEGT'-cb was prepared essentially as described for pYcDE8'-cb (Example 12E), with the following variations: The COS ends of 150 μg of λVEGT' were ligated (Maniatis et al., ibid) with T4 DNA ligase in a reaction volume of 200 μl. The ligase was heat killed with incubation at 65° C. for 15 minutes. The DNA was digested with Eco RI under conditions recommended by the enzyme manufacturer in a reaction volume of 1 ml. After incubation with 300 U of Eco RI for 2 hours, a second 300 U of enzyme was added, and incubation was continued for 2 more hours. The vector was phenol-chloroform extracted and ethanol precipitated. The exonuclease treatment with T4 DNA polymerase was carried out as described in Example 12, except that the reaction volume was 300 μl and 30 U of T4 DNA polymerase was used.

The globin and HepG2 cDNAs were prepared for directional cloning into λ prime vectors as described in Example 12. After preparation of the cut-back cDNAs, the cDNAs were ligated with 0.5 μg of λVEGT'-cb in 3 μl of 50 mM Tris-HCl pH 7.8, 5 mM MgCl$_2$, 1 mM ATP, 10 mM DTT, 0.3 Weiss U of T4 DNA ligase at 37° C. for 3 hours. After packaging and plating, the cloning efficiencies were $3.5 \times 10^6$ and $3.1 \times 10^6$ plaques per μg of vector for globin and HepG2 cDNA, respectively.

These libraries where analyzed for quality of cDNA inserts by probing plaque lifts of the libraries and Southern blots of DNA from the libraries using the method of Hagen et al. (*Biotechniques* 6:340-346 1988). 97% of the plaques from the globin library hybridized to a globin cDNA probe. 0.1% of the plaques of the HepG2 library hybridized to an actin cDNA probe, which is an expected number for this HepG2 RNA (Hagen et al., ibid). These numbers indicate that appropriate sequences representing starting mRNAs were inserted into the cloning vector. Southern blot analysis (Hagen et al. ibid) of DNA from these libraries using globin and actin cDNA probes produced bands at the expected sizes for full-length globin and actin cDNAs, indicating that the quality of cDNA synthesis was very good.

EXAMPLE 14

Releasing Plasmid Clones from λ Plasmid Prime Constructions

Plasmids residing in λ vectors are released with a method called "λ-pop". Although a λ vector containing a mammalian expression unit may be transfected directly into mammalian cells for expression of a cDNA (Okayama and Berg. *Mol. Cell. Biol.* 5: 1136-1142, 1985), transfection of plasmids allows for the utilization of much larger pool sizes. Second, while in vitro transcription of RNA from a phage promoter contained within λ-plasmid DNA is possible, much more specific RNA is obtained with transcription of a plasmid DNA. In addition, cDNA clones obtained from a λ-plasmid library may be subcloned using the λ-pop procedure.

The λ-pop procedure was applied to a library constructed in λvEG' (λVEGT' without the poly A sequence) using poly (A)+RNA from human HL-60 cells. 10 μg of DNA from this library was digested with 30 U of Not I in a 30 μl reaction. The DNA was diluted 10-fold and ligated with T4 DNA ligase. After phenol-chloroform extraction and ethanol precipitation, the DNA was electroporated (using a BioRad Gene Pulser and Pulse Controller) into XL-1 blue cells. This produced $1.7 \times 10^7$ colonies per μg of λ DNA starting material, or an equivalent of $1.8 \times 10^8$ colonies per μg of plasmid contained in the λ DNA.

EXAMPLE 15

Demonstration of Directional Cloning

To demonstrate that cDNA cloned by the directional cloning method is actually cloned in one orientation, single-stranded DNA from globin/pVEG' clones from the experiment described in Example 14 was prepared as described by Vieira and Messing (*Methods Enzymol.* 153: 3-11, 1987). Cultures inoculated from independent colonies were infected With M13 helper phage. After 12 hours of growth, the cells were pelleted by centrifugation. The supernatant was dot blotted in triplicate. These blots were probed with sense or anti-sense globin oligonucleotides or an oligonucleotide complementary to the anti-sense strand of the vector sequences. Results of this dot blot demonstrated that the globin cDNAs were directionally cloned.

From the foregoing it will be appreciated that, although specific embodiments of the invention have been described herein for purposes of illustration, various modifications may be made without deviating from the spirit and scope of the invention. Accordingly, the invention is not to be limited except as by the appended claims.

I claim:

1. A method for preparing a double-stranded DNA molecule, said molecule containing double-stranded cDNA consisting of a sense strand and an anti-sense strand, each of said strands having a 5' end and a 3' end, comprising the steps of:

annealing mRNA to a first oligodeoxynucleotide primer of the sequence $X_1T_n$, wherein $X_1$ is a sequence of deoxynucleotide monophosphates other than deoxythymidine from about 3 to about 25 nucleotides in length, wherein T is deoxythymidine monophosphate and wherein n is an integer from 6 to 30;

extending $X_1T_n$ with reverse transcriptase to produce an anti-sense strand;

adding deoxynucleotide monophosphates to the 3' end of said anti-sense strand to produce deoxynucleotide-tailed DNA;

annealing said deoxynucleotide-tailed DNA to a second oligodeoxynucleotide primer of the sequence $X_2T_yN_m$, wherein $X_2$ is a sequence of deoxynucleotide monophosphates other than deoxythymidine from about 3 to about 25 nucleotides in length, wherein N is a deoxynucleotide monophosphate complementary to the deoxynucleotide tail on said anti-sense strand, wherein m is an integer from 6 to 30, wherein T is deoxythymidine monophosphate and wherein y is an integer greater than or equal to 1;

extending $X_2T_yN_m$ with DNA polymerase to produce double-stranded cDNA;

treating said double-stranded cDNA with a DNA polymerase having 3'-exonuclease activity in the presence of deoxyadenosine triphosphate to remove the portions of the 3' ends of said double-stranded cDNA which are complementary to $X_1$ and $X_2$; and incubating said treated, double-stranded cDNA and a double-stranded linear vector in the presence of DNA ligase under conditions allowing hybridization and ligation of the cDNA and vector, said vector having 5' single stranded termini sufficiently complementary to $X_1$ and $X_2$ to allow annealing under the incubation conditions, wherein $X_1$ and $X_2$ are non-palindromic, sufficiently noncomplementary to prevent them from annealing to each other and sufficiently different to anneal to the vector in the desired orientation.

2. The method of claim 1 wherein said vector comprises a transcriptional promoter positioned so as to be capable, after the incubating step, of initiating transcription from said sense strand of said cDNA.

3. The method of claim 2 wherein said vector further comprises a transcriptional terminator positioned so as to be capable, after the incubating step, of terminating transcription from said sense strand of said cDNA.

4. The method of claim 3 wherein said terminator is a bacteriophage polymerase terminator.

5. The method of claim 4 wherein said terminator is selected from the group consisting of the bacteriophage T7, Sp6 and T3 terminators.

6. The method of claim 3 wherein said vector comprises two transcriptional terminators in tandem.

7. The method of claim 2 wherein said promoter is a bacteriophage polymerase promoter.

8. The method of claim 7 wherein said promoter is selected from the group consisting of the bacteriophage T7, Sp6 and T3 promoters.

9. The method of claim 2 wherein said vector further comprises a polyadenylation sequence positioned so as to be capable, after the incubating step, of directing the addition of a poly A tail to mRNA transcribed from said sense strand of said DNA.

10. The method of claim 1 wherein $X_1$ is GACAGAGCACAGAA and $X_2$ is AGGGAGACCGGAA.

11. The method of claim wherein said vector is a plasmid.

12. The method of claim wherein said vector is a λ bacteriophage or a derivative thereof.

13. The method of claim wherein said vector is selected from the group consisting of pVEGT' λVEGT', λgt11', pYCDE8' and pDVEG'.

14. The method of claim 1 wherein n=15.

15. The method of claim 1 wherein m=10.

16. The method of claim 1, further comprising, after the step of extending $X_1T_n$:
hydrolyzing the mRNA by treatment with alkali; and
fractionating the anti-sense strand DNA to remove fragments smaller than about 400 bases in length.

17. The method of claim 1 wherein the DNA polymerase used in the step of extending $X_2T_yN_m$ is selected from the group consisting of E. coli DNA polymerase I, the Klenow fragment of DNA polymerase I, T7 DNA polymerase and Taq 1 DNA polymerase.

18. The method of claim 1 wherein y is at least 2.

19. The method of claim 1 wherein said oligo d(T)-selected mRNA.

20. The method of claim 1 wherein the 3' end of said anti-sense strand is tailed with deoxyguanosine monophosphates and N is deoxycytidine monophosphate.

21. The method of claim wherein said DNA polymerase having 3'-exonuclease activity is T4 DNA polymerase.

22. A method of amplifying a population of mRNA molecules, comprising the steps of:
annealing said mRNA molecules to a first oligodeoxynucleotide primer of the sequence $X_1T_n$, wherein $X_1$ is a sequence of deoxynucleotide monophosphates other than deoxythymidine from about 3 to about 25 nucleotides in length, wherein T is deoxythymidine monophosphate and wherein n is an integer from 6 to 30;
extending $X_1T_n$ with reverse transcriptase to produce anti-sense cDNA;
adding deoxynucleotide monophosphates to the 3' end of said anti-sense cDNA to produce deoxynucleotide-tailed DNA;
annealing said deoxynucleotide-tailed DNA to a second oligodeoxynucleotide primer of the sequence $X_2T_yN_m$, wherein $X_2$ is a sequence of deoxynucleotide monophosphates other than deoxythymidine from about 3 to about 25 nucleotides in length, wherein N is a deoxynucleotide monophosphate complementary to the deoxynucleotide tail on said deoxynucleotide-tailed DNA, wherein m is an integer from 6 to 30, wherein T is deoxythymidine monophosphate and wherein y is an integer greater than or equal to 1;
extending $X_2T_yN_m$ with DNA polymerase to produce double-stranded cDNA;
treating said double-stranded cDNA with a DNA polymerase having 3'-exonuclease activity in the presence of deoxyadenosine triphosphate to remove the portions of the 3' ends of said double-stranded cDNA which are complementary to $X_1$ and $X_2$;
incubating said treated, double-stranded cDNA and a double-stranded linear vector in the presence of DNA ligase under conditions allowing hybridization and ligation of the cDNA and vector, said vector having 5' single-stranded termini sufficiently complementary to $X_1$ and $X_2$ to allow annealing under the incubation conditions, said vector further comprising a transcriptional promoter positioned so as to be capable, after ligation of the cDNA and vector, of initiating transcription from the sense strand of the double-stranded cDNA molecule;
inserting said annealed, double-stranded cDNA and vector into bacterial host cells; and
culturing said host cells under suitable conditions so that said cDNA is transcribed to produce mRNA, wherein $X_1$ and $X_2$ are non-palindromic, sufficiently noncomplementary to prevent them from annealing to each other and sufficiently different to anneal to the vector in the desired orientation.

23. The method of claim 22 wherein said promoter is a bacteriophage polymerase promoter.

24. The method of claim 23 wherein said promoter is selected from the group consisting of the bacteriophage T7, Sp6 and T3 promoters.

25. The method of claim 22 wherein said vector further contains a transcriptional terminator positioned so as to be capable, after ligation of the cDNA and vector, of terminating transcription from the sense strand of the cDNA.

26. The method of claim 25 wherein said terminator is a bacteriophage polymerase terminator.

27. The method of claim 26 wherein said terminator is selected from the group consisting of bacteriophage T7, Sp6 and T3 terminators.

28. The method of claim 25 wherein said vector comprises two transcriptional terminators in tandem.

29. The method of claim 22 wherein said vector further comprises a polyadenylation sequence positioned so as to be capable, after ligation of the cDNA and vector, of directing the addition of a poly A tail to mRNA transcribed from the sense strand of the double-stranded DNA.

30. The method of claim 22 wherein $X_1$ is GACA-GAGCACAGAA and $X_2$ is AGGGAGACCGGAA.

31. The method of claim 22 wherein said vector is a plasmid

32. The method of claim 22 wherein said vector is a λ bacteriophage or a derivative thereof.

33. The method of claim 22 wherein said vector is λgt11'.

34. The method of claim 22 wherein n=15.

35. The method of claim 22 wherein m=10.

36. The method of claim 22, further comprising, after the step of extending $X_1T_n$:
hydrolyzing the mRNA by treatment with alkali; and
fractionating the anti-sense strand DNA to remove fragments smaller than about 400 bases in length.

37. The method of claim 22 wherein the DNA polymerase used in the step of extending $X_2T_yN_m$ is selected from the group consisting of E. coli DNA polymerase I, the Klenow fragment of DNA polymerase I, T7 DNA polymerase and Taq 1 DNA polymerase.

38. The method of claim 22 wherein y is at least 2.

39. The method of claim 22 wherein said mRNA molecules are oligo d(T)-selected mRNA.

40. The method of claim 22 further comprising, prior to the step of inserting, heating said annealed, double-stranded cDNA and vector to denature contaminating DNA ligase.

41. The method of claim 22 wherein the 3' end of said anti-sense cDNA is tailed with deoxyguanosine monosphosphates, and N is deoxycytidine monophosphate.

42. The method of claim 22 wherein said DNA polymerase having 3'-exonuclease activity is T4 DNA polymerase.

43. A method of amplifying a population of mRNA molecules, comprising the steps of:
annealing said mRNA molecules to a first oligodeoxynucleotide primer of the sequence $X_1T_n$, wherein $X_1$ is a sequence of deoxynucleotides other than deoxythymidine from about 3 to about 25 nucleotides in length, wherein T is deoxythymidine and wherein n is an integer from 6 to 30;
extending $X_1T_n$ with reverse transcriptase to produce anti-sense cDNA;
adding deoxynucleotide monophosphates to the 3' end of said anti-sense cDNA to produce deoxynucleotide-tailed DNA;
annealing said deoxynucleotide-tailed DNA to a second oligodeoxynucleotide primer of the sequence $X_2T_yN_m$, wherein $X_2$ is a sequence of deoxynucleotide monophosphates other than deoxythymidine from about 3 to about 25 nucleotides in length, wherein N is a deoxynucleotide monophosphate complementary to the deoxynucleotide tail on said deoxynucleotide-tailed DNA, wherein m is an integer from 6 to 30, wherein T is deoxythymidine monophosphate and wherein y is an integer greater than or equal to 1;
extending $X_2T_yN_m$ with DNA polymerase to produce double-stranded cDNA;
treating said double-stranded cDNA with a DNA polymerase having 3'-exonuclease activity in the presence of deoxyadenosine triphosphate to remove the portions of the 3' ends of said double-stranded cDNA which are complementary to $X_1$ and $X_2$;
incubating said treated, double-stranded cDNA and a double-stranded linear vector in the presence of DNA ligase under conditions allowing hybridization and ligation of the cDNA and vector, said vector having 5, single-stranded termini sufficiently complementary to $X_1$ and $X_2$ to allow annealing under the incubation conditions, said vector further comprising a transcriptional promoter positioned so as to be capable, after ligation of the cDNA and vector, of initiating transcription from the sense strand of the double-stranded cDNA;
inserting said annealed, double-stranded cDNA and vector into bacterial host cells;
culturing said host cells to amplify the cDNA and vector;
extracting said cDNA and vector from said host cells; and
transcribing said cDNA to produce mRNA, wherein $X_1$ and $X_2$ are non-palindromic, sufficiently non-complementary to prevent them from annealing to each other and sufficiently different to anneal to the vector in the desired orientation.

44. The method of claim 43 wherein said transcribing step comprises in vitro transcription.

45. The method of claim 44 wherein said vector is pVEGT' or λVEGT'.

46. The method of claim 44 wherein said promoter is a bacteriophage polymerase promoter.

47. The method of claim 46 wherein said promoter is selected from the group consisting of the bacteriophage T7, Sp6 and T3 promoters.

48. The method of claim 43 wherein said vector further contains a transcriptional terminator positioned so as to be capable, after ligation of the cDNA and vector, of terminating transcription from the sense strand of the cDNA.

49. The method of claim 48 wherein said terminator is a bacteriophage polymerase terminator.

50. The method of claim 49 wherein said terminator is selected from the group consisting of bacteriophage T7, Sp6 and T3 terminators.

51. The method of claim 43 wherein said vector comprises two transcriptional terminators in tandem.

52. The method of claim 43 wherein said vector further comprises a polyadenylation sequence positioned so as to be capable, after ligation of the cDNA and vector, of directing the addition of a poly A tail to mRNA transcribed from the sense strand of the double-stranded DNA.

53. The method of claim 43 wherein $X_1$ is GACA-GAGCACAGAA and $X_2$ is AGGGAGACCGGAA.

54. The method of claim 43 wherein n=15.

55. The method of claim 43 wherein m=10.

56. The method of claim 43, further comprising, after the step of extending $X_1T_n$:
hydrolyzing the mRNA by treatment with alkali; and
fractionating the anti-sense strand DNA to remove fragments smaller than about 400 bases in length 57. The method of claim 43 wherein the DNA polymerase used in the step of extending $X_2T_yN_m$ is selected from the group consisting of E. coli DNA polymerase I, the Klenow fragment of DNA polymerase I, T7 DNA polymerase and Taq 1 DNA polymerase.

58. The method of claim 43 wherein y is at least 2.

59. The method of claim 43 further comprising, prior to the step of inserting, heating said annealed, double-stranded cDNA and vector to denature contaminating DNA ligase.

60. The method of claim 43 wherein the 3' end of said anti-sense cDNA is tailed with deoxyguanosine monophosphates, and N is deoxycytidine monophosphate.

61. The method of claim 43 wherein said DNA polymerase having 3'-exonuclease activity is T4 DN polymerase.

62. The method of claim 43, wherein said transcribing step comprises inserting the extracted cDNA and vector into eukaryotic host cells and culturing said eukaryotic host cells so that said cDNA is transcribed to produce mRNA.

63. The method of claim 62, wherein said eukaryotic host cells are yeast cells or cultured mammalian cells.

64. The method of claim 62, wherein said vector is pYcDE8' or pDVEG'.

65. The vector pVEGT'.

66. The vector λVEGT'.

* * * * *

UNITED STATES PATENT AND TRADEMARK OFFICE
CERTIFICATE OF CORRECTION

PATENT NO. : 5,075,227

DATED : December 24, 1991

INVENTOR(S) : Frederick S. Hagen

It is certified that error appears in the above-identified patent and that said Letters Patent is hereby corrected as shown below:

In column 21, claim 11, line 33, after "claim" please insert -- 1 --.

In column 21, claim 12, line 35, after "claim" please insert -- 1 --.

In column 21, claim 13, line 37, after "claim" please insert -- 1 --.

In column 21, claim 19, line 53, after "said" please insert -- mRNA is --.

In column 21, claim 21, line 58, after "claim" please insert -- 1 --.

In column 24, claim 43, line 5, please delete "5," and substitute therefor -- 5' --.

In column 25, claim 61, line 5, please delete "DN" and substitute therefor -- DNA --.

Signed and Sealed this

Twenty-third Day of March, 1993

Attest:

STEPHEN G. KUNIN

*Attesting Officer*  *Acting Commissioner of Patents and Trademarks*

UNITED STATES PATENT AND TRADEMARK OFFICE
CERTIFICATE OF CORRECTION

PATENT NO. : 5,075,227  Page 1 of 2
DATED : December 24, 1991
INVENTOR(S) : Frederick S. Hagen It is certified that error appears in the above-identified patent and that said Letters Patent is hereby corrected as shown below:

In column 4, line 8, please delete "insert" and substitute therefor -- insertion of --.

In column 4, line 11, please insert a space after "T1".

In column 5, lines 31 and 38, please delete "$H^{31}$" and substitute therefor -- $H^-$ "

In column 6, line 57, please delete "polymerase" and substitute therefor -- polymerases --.

In column 6, line 61, after "United" please insert --States--.

In column 8, line 16, please delete "pDVEG40" and substitute therefor --pDVEG'--.

In column 8, line 44, please delete "palmiter" and substitute therefor -- Palmiter --.

UNITED STATES PATENT AND TRADEMARK OFFICE
CERTIFICATE OF CORRECTION

PATENT NO.　:　5,075,227　　　　　　Page 2 of 2

DATED　　　:　December 24, 1991

INVENTOR(S) :　Frederick S. Hagen

It is certified that error appears in the above-identified patent and that said Letters Patent is hereby corrected as shown below:

In column 9, line 37, after MgCl$_2$" and before "mM", please insert -- 2 --.

In column 14, line 22, please delete "pVEGT" and substitute therefor -- pVEGT'"

In column 15, line 25, please delete "Was" and substitute therefor -- was --.

In column 18, line 60, please delete "$\mu$" and substitute therefor -- $\lambda$ --.

In column 19, line 58, please delete "$\lambda$vEG'" and substitute therefor -- $\lambda$VEG' --.

In column 20, line 11, please delete "With" and substitute therefor -- with --.

Signed and Sealed this

Twenty-second Day of June, 1993

Attest:

MICHAEL K. KIRK

*Attesting Officer*　　　Acting Commissioner of Patents and Trademarks